US012372509B2

(12) United States Patent
Lavely et al.

(10) Patent No.: US 12,372,509 B2
(45) Date of Patent: Jul. 29, 2025

(54) CORRECTION OF INTERNAL WAVE EFFECTS ON A PROPAGATING ACOUSTIC SIGNAL

(71) Applicant: BAE Systems Information and Electronic Systems Integration Inc., Nashua, NH (US)

(72) Inventors: Eugene M. Lavely, Concord, MA (US); Peter B. Weichman, Bedford, MA (US)

(73) Assignee: BAE Systems Information and Electronic Systems Integration Inc., Nashua, NH (US)

( * ) Notice: Subject to any disclaimer, the term of this patent is extended or adjusted under 35 U.S.C. 154(b) by 853 days.

(21) Appl. No.: 17/285,621

(22) PCT Filed: Sep. 17, 2019

(86) PCT No.: PCT/US2019/051466
§ 371 (c)(1),
(2) Date: Apr. 15, 2021

(87) PCT Pub. No.: WO2024/043865
PCT Pub. Date: Feb. 29, 2024

(65) Prior Publication Data
US 2024/0003862 A1 Jan. 4, 2024

(51) Int. Cl.
G01N 33/18 (2006.01)
G01C 13/00 (2006.01)
(Continued)

(52) U.S. Cl.
CPC ......... G01N 33/1886 (2013.01); G01C 13/00 (2013.01); G01C 13/002 (2013.01);
(Continued)

(58) Field of Classification Search
CPC ............... G01N 33/1886; G01N 33/18; G01N 29/4463; G01C 13/00; G01C 13/002; G01S 1/72; G01S 3/8083
See application file for complete search history.

(56) References Cited

U.S. PATENT DOCUMENTS 5,119,341 A     6/1992  Youngberg
5,568,450 A  * 10/1996  Grande ................. H04B 13/02
                                                    367/131
(Continued)

FOREIGN PATENT DOCUMENTS

CN    202092644 U      12/2011
CN    203520622 U  *   4/2014
CN    108216492 A  *   6/2018  ............. B63B 22/00

OTHER PUBLICATIONS

International Search Report, PCT/US19/51451, mailed Jun. 2, 2020, 17 pages.
(Continued)

Primary Examiner — David Z Huang
(74) Attorney, Agent, or Firm — Scott J. Asmus; Gary McFaline

(57) ABSTRACT

An underwater sensing system includes a cable structure, a water surface mount coupled to the cable structure, and a processor. The cable structure is configured to be deployed in a vertical orientation underwater and includes one or more sensors along a length of the cable structure. The one or more sensors are configured to detect maritime data associated with one or more marine-based parameters in an underwater maritime region around the cable structure. The water surface mount is configured to be at least partially exposed above a surface of the underwater maritime region and includes a transmitter configured to transmit the maritime data. The processor is configured to access a maritime model comprising parameters associated with the maritime (Continued)

region and update the maritime model based on the maritime data. The maritime model can be used as an input, or otherwise made accessible, to a navigation system of an underwater vehicle.

19 Claims, 7 Drawing Sheets

(51) Int. Cl.
    *G01N 29/44*     (2006.01)
    *G01S 1/72*     (2006.01)
    *G01S 3/808*     (2006.01)

(52) U.S. Cl.
    CPC ......... *G01N 29/4463* (2013.01); *G01N 33/18* (2013.01); *G01S 1/72* (2013.01); *G01S 3/8083* (2013.01)

(56) References Cited

U.S. PATENT DOCUMENTS

| | | |
|---|---|---|
| 10,379,218 B1 | 8/2019 | Spiesberger |
| 2006/0235583 A1 | 10/2006 | Larsen |
| 2007/0019505 A1 | 1/2007 | Lohrmann et al. |
| 2008/0008045 A1 | 1/2008 | Basilico |
| 2008/0198695 A1 | 8/2008 | Abdi |
| 2009/0196122 A1 | 8/2009 | Crowell |
| 2009/0269709 A1* | 10/2009 | Fowler .................. B63B 22/04 431/1 |
| 2010/0085839 A1 | 4/2010 | Rhodes et al. |
| 2010/0110835 A1 | 5/2010 | Rhodes et al. |
| 2012/0092964 A1 | 4/2012 | Badiey et al. |
| 2012/0243375 A1 | 9/2012 | Melvin, II et al. |
| 2014/0300885 A1 | 10/2014 | Debrunner et al. |
| 2015/0078123 A1 | 3/2015 | Batcheller et al. |
| 2016/0086093 A1 | 3/2016 | Forero et al. |
| 2016/0349387 A1 | 12/2016 | Rokkan et al. |
| 2016/0364990 A1 | 12/2016 | Khaghani et al. |
| 2017/0183068 A1 | 6/2017 | Suunto |
| 2017/0227638 A1 | 8/2017 | Nicoletti et al. |
| 2018/0074195 A1 | 3/2018 | Wiegers |

OTHER PUBLICATIONS

International Search Report, PCT/US19/51455, mailed Jul. 23, 2020, 13 pages.
International Search Report, PCT/US19/51456, mailed Jul. 15, 2020, 13 pages.
International Search Report, PCT/US19/51459, mailed May 28, 2020, 9 pages.
International Search Report, PCT/US19/51462, mailed Jun. 9, 2020, 21 pages.
International Search Report, PCT/US19/51465, mailed Jun. 9, 2020, 12 pages.
International Search Report, PCT/US19/51466, mailed Jun. 3, 2020, 11 pages.

* cited by examiner

CORRECTION OF INTERNAL WAVE EFFECTS ON A PROPAGATING ACOUSTIC SIGNAL

GOVERNMENT LICENSE RIGHTS

This invention was made with government support under contract #N66001-16-C-4001 awarded by the Defense Advanced Research Projects Agency (DARPA). The government has certain rights in the invention.

RELATED APPLICATIONS

This application is related to the following U.S. application Ser. No. 17/285,514 entitled "Precomputed Acoustic Fields for Underwater Navigation" filed concurrently with this application; U.S. application Ser. No. 17/285,519 entitled "System and Method for Position, Navigation, and Timing for Undersea Vehicles" filed concurrently with this application; U.S. application Ser. No. 17/285,527 entitled "Maritime Model Generation Using Acoustics" filed concurrently with this application; U.S. application Ser. No. 17/285,592 entitled "Maritime Model Updating using Surface Quasigeostrophic Theory" filed concurrently with this application; U.S. application Ser. No. 17/285,601 entitled "Underwater Tracking Using Dynamic Modeling" filed concurrently with this application; and U.S. application Ser. No. 17/285,611 entitled "Doppler-Aided Underwater Tracking" filed concurrently with this application.

BACKGROUND

The global positioning system (GPS) is the predominant means of obtaining position, navigation, and timing (PNT) information for both military and civilian systems and applications. However, the electromagnetic radio frequency (RF) basis for GPS also means that its signals cannot penetrate seawater due to the small skin-depth of such waves, and thus undersea GPS is effectively denied. Undersea vehicles typically use inertial measurement units (IMU) and other dead reckoning sensors to navigate while submerged, wherein the underwater navigation is based on the last known GPS coordinates or other surface-captured position fix. While dead reckoning sensors may provide navigation for short duration missions using on-board resources alone, accumulation of inertial error eventually requires measurements of externally generated data to maintain or restore accurate performance. Significant positioning error may be incurred in a matter of minutes or even seconds for low or even moderate cost IMUs, and therefore such IMUs cannot support realistic mission durations. As a result, most undersea vehicles must regularly surface to receive GPS signals and thereby generate an updated position fix. This need to resurface presents a risk of detection (loss of covertness), reduces mission efficiency, and expends resources. High performance underwater vehicles such as advanced submarines use high performance IMUs, enabling extended periods of high accuracy underwater navigation. Unfortunately, in many applications the cost of such sensors is not feasible or realistically matched to the cost of the underwater vehicle (or platform). High-performing IMU systems may also have heavy power draws, which is undesirable on many vehicles. Data from other navigation aids such as Doppler Velocity Logs (DVLs) can be combined with IMU measurements for improved navigation accuracy. However, DVLs consume power resources that can adversely impact mission duration, and perhaps more significantly may compromise mission covertness due to their use of active sonar.

BRIEF DESCRIPTION OF THE DRAWINGS

Features and advantages of embodiments of the claimed subject matter will become apparent as the following Detailed Description proceeds, and upon reference to the Drawings, in which:

Figure 1:
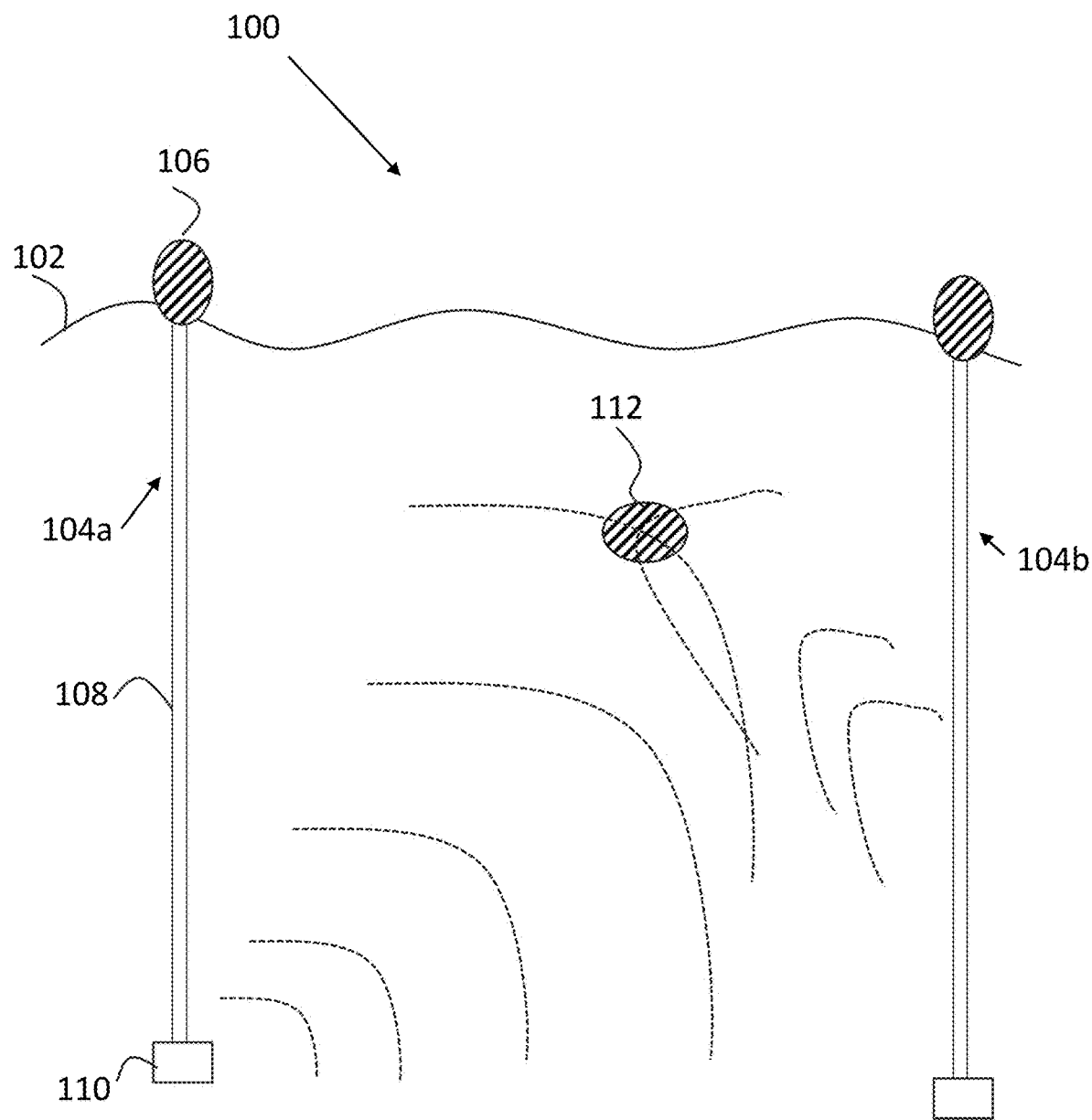
FIG. 1 illustrates an example underwater acoustic signaling environment, in accordance with some embodiments of the present disclosure.

Although the following Detailed Description will proceed with reference being made to illustrative embodiments, many alternatives, modifications, and variations thereof will be apparent in light of this disclosure.

DETAILED DESCRIPTION

An underwater sensing system is disclosed. Although a number of applications of the system will be appreciated in light of this disclosure, the system is particularly well-suited for correction of internal wave effects on a propagating acoustic signal. In an embodiment, the system includes a cable structure, a water surface mount coupled to the cable structure, and a processor. The cable structure is configured to be deployed in a vertical orientation underwater and includes one or more sensors along a length of the cable structure. The one or more sensors are configured to detect maritime data associated with one or more marine-based parameters (e.g., water temperature, salt content, pressure, and velocity) in an underwater maritime region around the cable structure. The water surface mount is configured to be at least partially exposed above a surface of the underwater maritime region and includes a transmitter configured to transmit the maritime data. The processor is configured to access a maritime model comprising parameters associated with the maritime region and update the maritime model based on the maritime data. The maritime model can be used as an input, or otherwise made accessible, to a navigation system of an underwater vehicle.

In a more general sense, methods and systems are disclosed for updating a maritime model to account for both short and long period underwater waves for underwater navigation. An underwater positioning system is disclosed that uses a plurality of signal beacons beneath the water's surface to geolocate an underwater vehicle using timed acoustic transmissions. Although specific such underwater configurations can vary from one embodiment to the next, some such configurations may, for example, (i) support an appropriate software architecture inclusive of but not limited to an underwater acoustic propagation model, (ii) receive and processes acoustic signals with receiver elements similar to those used in hydrophone arrays, and (iii) perform attribution of a receiver signal to known signal beacon(s) and beacon location(s). By measuring the absolute range to multiple signal beacons, an undersea platform or vehicle can obtain continuous, accurate positioning without surfacing for a GPS fix.

The time-of-flight calculations for sound waves in the water are dependent on numerous variables associated with the surrounding water. Both long-period and short-period internal waves are a key limiting factor for ranging and positioning accuracy in acoustics-based undersea positioning. Internal waves are characterized by a buoyancy driven restoring force. The vertical component of the wave action entrains fluid parcels, thereby dynamically altering the thermodynamic vertical stratification of the water column. Internal waves effectively change the maritime reference model and therefore perturb acoustic wave propagation. The spatial and temporal scales of this perturbation correspond to the spatial and temporal spectrum of the internal waves. In one perspective their effect can be viewed as a dynamical fluctuation of the model relative to the more slowly varying spatial and temporal evolution of the maritime state attributable to the general circulation. Long period internal waves may have wavelengths spanning from ~100 km to thousands of kilometers, and have periods from one minute to twelve hours, while short-period internal waves may have wavelengths spanning from ~1 m to about 10 kilometers and have periods from one second to about 30 seconds. These waves (or modes) introduce spatio-temporal dynamical fluctuations to the medium, and add vertical spatial scales corresponding to the internal mode eigenfunction shapes. The superposition of these dynamical disturbances is observed as a net perturbation to a reference maritime model leading to local changes in various parameters such as temperature, pressure and salinity. As these quantities are used to define the local sound speed, the travel time and specific ray paths associated with acoustic modes are perturbed. Therefore, if unaccounted for, these long and short period internal wave effects change the "predicted" acoustic signals relative to actual acoustic measurements that encode these effects. Acoustic data acquired on an undersea vehicle or a target platform and subsequently processed for tracking or positioning information will be subject to bias or error absent correction of the internal wave perturbation to the recorded data.

The short-period internal waves are a part of a continuum spectrum of internal waves, roughly described by and consistent with the Garrett-Munk spectrum defining the energy distribution of internal waves as a function of frequency and spatial wavelength. While all components of the internal wave spectrum will affect acoustic propagation, the estimation, modeling and correction for the short-period internal waves on positioning, navigation and timing (PNT) systems is difficult as it tends to be impractical to measure experimentally the short-period internal waves to the fine-scale that would be required for deterministic, model-based correction. However, physics-based methods that utilize the statistics of the fluctuations represent an alternative approach, as they do not require detailed, densely collected, spatially distributed measurements. Instead, the statistical approach may be used to account for the short-period internal waves on acoustic waves using an experimentally sparse set of measurements, use of the parameters of the reference maritime model, and appropriate processing, as discussed in further detail herein.

Accordingly, accurately accounting for the perturbative effect of long and short period internal waves within a given maritime region enables adjustment of the parameters influencing acoustic propagation that may be used, in turn, to compute and remove the effect of internal waves on the acoustic data. Absent other effects, this removes the bias otherwise introduced by internal waves when performing acoustics-based geolocation. The model defines the standard prognostic variables used in maritime circulation simulation and estimation, including temperature, salinity, meridional and zonal components of the velocity field, and the sea surface height. These parameters may be transformed into the acoustic reference model parameters that define acoustic signal propagation through the corresponding maritime region. The model may have an initial state based on the best estimate of the current state of the various maritime parameters. Alternatively, the initial model may have a future forecast state, or a state in the recent past estimated with data collected in an interval spanning a time prior to that past date and up to the current time. The maritime model may be loaded into an underwater vehicle for subsequent access by an onboard processor when predicting the time-of-fight (TOF) (or full waveforms) of various received acoustic signals from spatially separated acoustic beacons. The various parameters that inform this model may be gathered from existing ocean basin models for distinct oceanic regions or from global models, such as the North Atlantic basin model. These models may be obtained as the outputs of highly sophisticated data assimilation computer codes in which models are constructed that simultaneously satisfy the constraints imposed by the equations of motion and the available data measurements e.g., both from point-based sensors and from satellites supporting various sensing modalities. One example model encoding the equations of motion is the Massachusetts Institute of Technology (MIT) general circulation model (MITgcm). It has been used in combination with the ECCO (Estimating the Circulation and Climate of the Ocean) assimilation method. The MITgcm encodes and numerically solves the equations of motions of a three-dimensional fluid parcel on the rotating sphere, consisting of conservation equations for momentum, volume, heat and salt, along with a nonlinear equation of state for seawater and appropriate initial, surface and bottom boundary conditions.

According to an embodiment, a sensor array may be disposed within a given maritime region to measure various parameters of the surrounding water such as temperature, salinity, pressure, etc. The effects of the long and short period internal waves on acoustic signal propagation can be derived based on changes over time to the various measured parameters from the sensor array.

According to an embodiment, an underwater sensing system includes a cable structure, a water surface mount coupled to the cable structure, and a processor. The cable structure is configured to be disposed in a vertical orientation underwater and includes one or more sensors disposed along a length of the cable structure. The one or more sensors are configured to measure maritime data associated with one or more marine-based parameters in a maritime region around the cable structure. The water surface mount is configured to be at least partially exposed above a surface of the water and includes a transmitter configured to transmit the maritime data. The processor is configured to access a maritime model comprising parameters associated with the maritime region and update the maritime model based on the maritime data.

According to another embodiment, a method of updating a maritime model to account for the effects of internal waves includes measuring maritime data associated with a maritime region using one or more sensors disposed underwater in the maritime region. The method also includes receiving model update parameters at a processing unit. The model update parameters are derived from the maritime data. The method also includes accessing, using the processing unit, a maritime model comprising parameters associated with the maritime region, and updating, using the processing unit, the maritime model using the model update parameters.

Numerous embodiments, variations, and applications will be appreciated in light of the disclosure herein.

General Overview

FIG. 1 illustrates an underwater acoustic propagation environment 100 in which a plurality of signal beacons (two of which are represented by 104a and 104b) are mostly located beneath the water's surface 102, according to some embodiments. The signal beacons 104a and 104b may be several hundred kilometers apart, or even several thousand kilometers apart, depending on the signaling strength required, the feasible (or tactically accessible) signal beacon locations available, or the required distribution for high-accuracy undersea vehicle localization e.g., the signal beacon distribution should minimize the geometric dilution of precision (GDOP) with respect to the probability distribution of intended (or likely) signal beacon locations. Each of signal beacons 104a and 104b includes the same (or at least functionally similar) components, and thus the components of only signal beacon 104a are discussed in more detail herein.

Signal beacon 104a includes a water surface mount 106, a cable structure 108, and a transducer system 110. Other elements not shown in FIG. 1 may be included as well. For example, cable structure 108 may also include a plurality of sensors along a length of cable structure 108, such as thermistors, for monitoring characteristics of the surrounding water including, for example, changes in the local temperature due to internal wave motions. Other sensors that may be used along cable structure 108 include pressure sensors, current velocity sensors, salinity sensors and acoustic receivers (e.g., hydrophones.)

Water surface mount 106 may be a buoy, a boat, or any floatation mechanism that remains above water surface 102. Note, however, that camouflage can be applied to mount 106, to actually make it difficult to see when stealth is important to a given application. In some embodiments, water surface mount 106 includes one or more RF receivers, transmitters, or transceivers for communicating data with, for example, a ship, aircraft, satellite, or a land-based communication station. Received data may include data associated with a maritime model or information update of a maritime model to be transmitted underwater by transducer system 110. Additional data may include specification of waveform type to transmit, pulse repetition frequency, transmission duty cycle, etc. Transmitted data may include data gathered from the plurality of sensors along the length of cable structure 108. Water surface mount 106 may include some form of power supply (e.g., batteries and/or solar panels) to provide power to any of the components of signal beacon 104a. In some other embodiments, rather than being buoy-based, water surface mount 106 represents a coupling, such as a winch, on a ship or waterborne platform that holds its position on water surface 102. A shipboard power supply, amplifier, and control electronics may then be used to interface with transducer system 110 and/or with any other electrical components of signal beacon 104a.

Cable structure 108 may include one or more signaling cables bundled together for transmitting electrical signals to (and possibly from) transducer system 110. The one or more signaling cables may also be used to transmit electrical signals to and from any other sensors or actuators present on signal beacon 104a. In some embodiments, cable structure 108 is made up of a plurality of segments that are connected together to form the total length of cable structure 108. Cable structure 108 may include a strength member amongst or surrounding the bundled cables to protect the signaling cables and to impart greater rigidity to cable structure 108.

In some embodiments, cable structure 108 is mounted to a weighted structure that sits on the ocean or sea bottom and extends up from the weighted structure to transducer system 110. In such embodiments, water surface mount 106 may still be used to provide RF signaling and GPS capabilities for signal beacon 104a. The weighted structure on the ocean or sea bottom may include a power supply and one or more processing devices for generating the acoustic waves to be transmitted by transducer system 110.

Transducer system 110 may include any type of electromechanical transducer that produces mechanical motion from an electrical input. The mechanical motion of an electromechanical transducer produces acoustic waves that propagate through the water. Transducer system 110 may include a sonar transducer or may include a plurality of sonar transducers. Any number of electromechanical transducers capable of transferring mechanical movement into sound waves that can travel through water can be used. Further details of transducer system 110 are provided with reference to FIG. 3.

An underwater vehicle 112 receives the acoustic signals generated from each of signal beacon 104a and 104b. Underwater vehicle 112 may be any kind of submerged vehicle or platform, such as an unmanned underwater vehicle (UUV), although manned underwater vehicles (e.g., submarines) can equally benefit as well as sensor probe packages equipped with acoustic receiver capability. For instance, in some manned underwater examples, a wearable device, such as by a scuba diver, receives the acoustic signals generated from each of signal beacon 104a and 104b, and uses the received signals to geolocate the wearable device in the same way as the underwater vehicle. Underwater vehicle 112 includes one or more acoustic receivers for receiving the acoustic signals transmitted through the water by any surrounding signal beacons, such as signal beacons 104a and 104b. According to some embodiments, each of signal beacons 104a and 104b transmits at scheduled intervals. This schedule is known to underwater vehicle 112 such that underwater vehicle 112 can determine when a received acoustic pulse was transmitted. According to some embodiments, the acoustic signals transmitted from signal beacons 104a and 104b utilize a waveform that minimizes the computational burden at the receiver on underwater vehicle 112 while maximizing the desired information content. For example, waveforms with low auto-correlation sidelobes improve the detection performance of weak arrivals as they maximize the signal-to-noise ratio (SNR) when accompanied by an appropriate receiver filter, while significantly weakening signals from adjacent time bins. Similarly, waveforms with low cross-correlations reduce multi-user interference.

Additionally, underwater vehicle 112 can determine which signal beacon transmitted a given received acoustic pulse based on one or more characteristics of the received acoustic pulse. In one example, signal beacons transmit acoustic pulses in different frequency bands such that the measured bandwidth of the received pulse is used by underwater vehicle 112 to determine which signal beacon the received pulse is associated with. In another example, each signal beacon transmits an acoustic pulse having a modulated code that is unique to each signal beacon. In this case, underwater vehicle 112 can demodulate the received acoustic pulse and interpret the code to determine which signal beacon the received pulse is associated with. In yet another example, each acoustic signal has a unique phase structure based on which signal beacon it is transmitted from. Accordingly, underwater vehicle 112 can be preloaded with knowledge about which phase structures are associated with which signal beacons. In yet another example, a pre-determined collection of continuous wave (CW) signals are transmitted by a given beacon, and whose values are "known" to the receiver. Such signals can be transmitted simultaneously with the pulsed signals, or sequentially, and for varying durations.

Since the onset transmission time of a received pulse from a given signal beacon is known, the range between the undersea vehicle and the signal source can be estimated using the measured data and if the varying acoustic sound speed of the propagation medium is known. In general, this sound speed model is presented in three dimensions and is time varying e.g., due to general circulation over the secular time scale and due to dynamical effects over shorter time scales e.g., tides, internal waves, etc. In practice, and for high-fidelity localization accuracy, other effects would also be considered such as frequency-dependent dispersion of the acoustic pulse as it propagates, refraction and multi-pathing, and other effects The sound speed depends on a plurality of parameters associated with a state (or states over time) of the water in the maritime region where underwater vehicle 112 is located as well as the water medium sampled by the acoustic waves between the vehicle itself and the signal beacon. A maritime model (or at least portions of a maritime model) may be preloaded into underwater vehicle 112 that includes numerous parameters to account for a variety of underwater effects on acoustic propagation. Underwater vehicle 112 may use the maritime model to determine the acoustic propagation from a given signal beacon, and thus determine a predicted acoustic waveform to be received from the given signal beacon. Using an appropriate metric, the predicted acoustic waveform can then be compared to the actual acoustic waveform received from the given signal beacon to estimate a range between underwater vehicle 112 and the given signal beacon. This process may be repeated for a plurality of signal beacons to geolocate underwater vehicle 112. In general, this process may be viewed as an optimization problem in which the search space includes the unknown position parameters of the vehicle/platform.

As noted above, the ranging estimate performed with respect to each signal beacon assumes that the location of the signal beacon is known and does not change. According to some embodiments, there are at least three options available to relax the latter assumption: (1) perturbations to the nominal position of the signal beacon(s) can be independently estimated and acoustically transmitted via a data waveform for more accurate ranging performed on the receive platform, (2) a new signal beacon (and location) may be introduced and information on its location and waveform type may be transmitted acoustically, and (3) a joint estimation for platform position and perturbed signal beacon locations for the model estimate most consistent with all of the available data. The model parameter set may include the platform location, the speed and bearing of the platform, the kinematic velocity history of the source beacon(s), nominal perturbations to the "known" reference position of the source beacon(s), and others. In some embodiments, signal beacons 104a and 104b use GPS to continually locate their position and are designed to transmit their current location to underwater vehicle 112. The location information may be included in any acoustic signal transmitted by transducer system 110 to be received by underwater vehicle 112. Both pulse waveform acoustic data and continuous wave (CW) acoustic data may be used to estimate the positions and kinematics of the source and the receiver. Pulse data can provide positioning information and repeat pulse transmissions over time define a sequence of position estimates that constrain kinematics, while CW data can provide continuously recorded Doppler data useful for continuous monitoring and updating of platform speed and bearing.

The maritime model loaded into underwater vehicle 112 includes a plurality of maritime parameters such as, for example, temperature, salinity, meridional and zonal velocity components of the general circulation, sea surface height, etc. According to an embodiment, one or more parameters of the maritime model may be updated to account for the effect of long-period internal waves using measurements taken from the surrounding maritime region.

Figure 2:
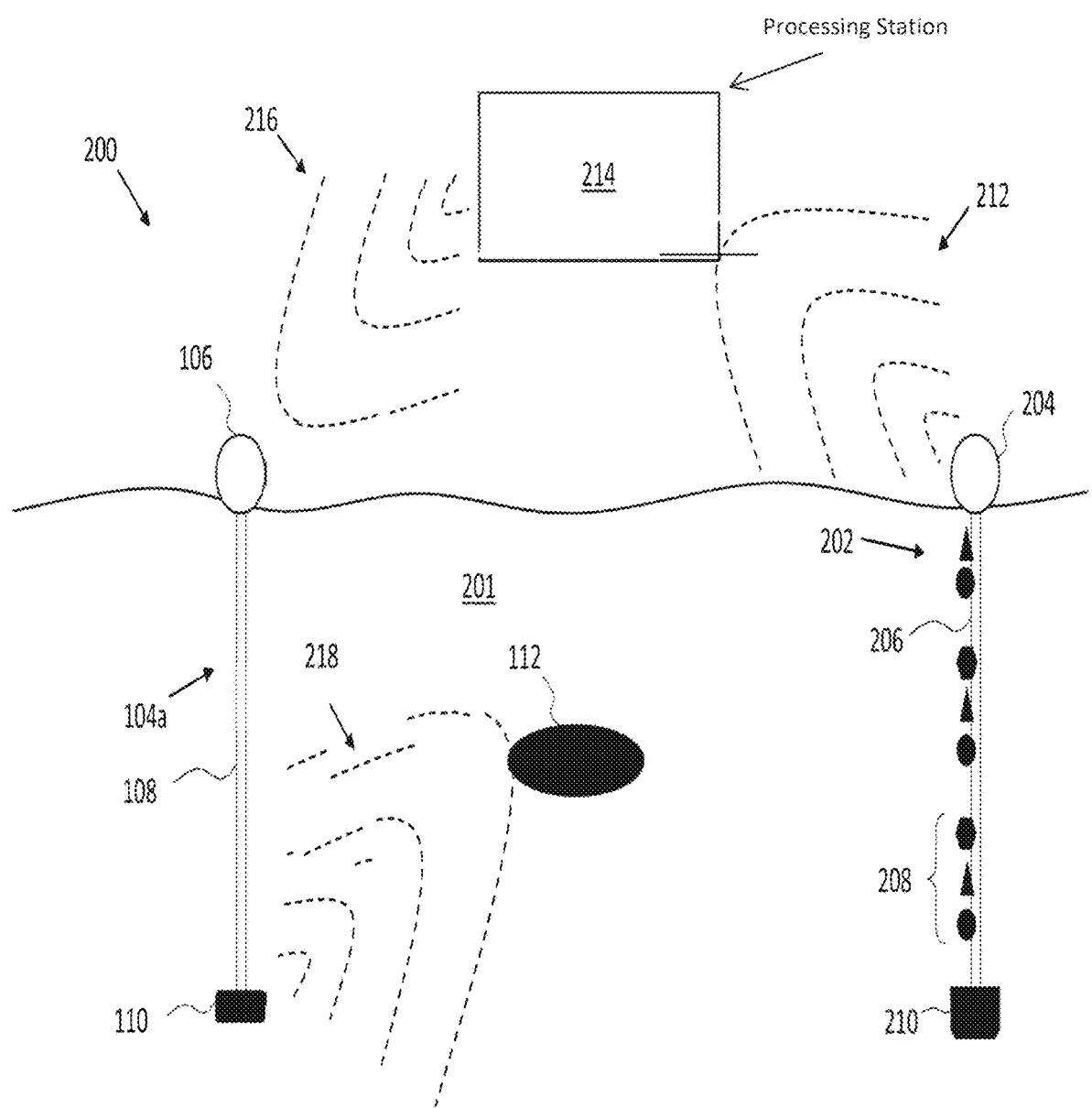
FIG. 2 illustrates an example underwater measuring environment, in accordance with some embodiments of the present disclosure.

FIG. 2 illustrates an underwater measuring environment 200 where a measurement apparatus 202 is partially (or fully) submerged beneath the water in a given maritime region 201. Maritime region 201 can represent any size region, but at minimum will define the maritime model parameters inclusive of the convex hull defined by the source(s) expected to be used for positioning and tracking and by the totality of the expected underwater vehicle 112 positions for current and/or anticipated missions. Thus, maritime parameter data may be collected by measurement apparatus 202 for particular regions of interest, in some embodiments.

Measurement apparatus 202 may include a water surface mount 204, a cable structure 206, a plurality of sensors 208, and a weight 210. Water surface mount 204 may be substantially similar to water surface mount 106, and thus the description above for water surface mount 106 can apply equally to water surface mount 204. In some embodiments, water surface mount 204 includes a spar buoy. Additionally, cable structure 206 may be substantially similar to cable structure 108, and thus the description above for cable structure 108 can apply equally to cable structure 206. A total length of cable structure 206 may be, for example, around 1000 m, according to some embodiments.

A plurality of sensors 208 may be arranged along a length of cable structure 206. Plurality of sensors 208 may include any number of various sensor types, or may include any number of a single sensor type. The types of sensors that may be included in plurality of sensors 208 include thermistors, salinity meters, pressure sensors, inclinometers, and velocimeters, to name a few examples. Accordingly, maritime-based parameters that may be measured include temperature, salt content, pressure, and velocity, to name a few examples. Acoustic receivers are an additional sensor type that may be featured in sensors 208. Such sensors may be used, for example, to record acoustic source transmissions from the other distributed sources in the positioning system, or from source signals separate from the positioning system. In one embodiment, the acoustic data is processed to determine variance in arrival times for pulsed sources. Such data may be transmitted to a global processing center for inference of corrections to the Garrett-Munk model. The sensors (non-acoustic and acoustic) may be arranged by type in a repeating pattern along the length of cable structure 206 to ensure that each type of sensor is provided at different depths. For example, a repeating pattern of thermistor, pressure sensor, salinity meter, velocimeter may be used along the length of cable structure 206. In some other embodiments, clusters of a single sensor type may be provided along the length of cable structure 206. Each of the plurality of sensors 208 may be electrically coupled with wires or other conductors within cable structure 206 to transmit measurements up to water surface mount 204. In one embodiment, each of the plurality of sensors 208 record and store measurement data locally, and the data may later be retrieved directly e.g., by raising the cable, or by some other means.

According to an embodiment, maritime data 212 is transmitted from water surface mount 204 using, for example, an RF transmitter. Any known transmission protocols may be used for transmitting maritime data 212. The maritime data 212 includes measured data associated with any number of plurality of sensors 208. In some embodiments, the measured data is processed, or reduced prior to transmission. In other embodiments, the data is compressed prior to transmission. In other embodiments, plurality of sensors 208 are polled periodically and the polled measurements are transmitted as maritime data 212. For example, measurements may be taken by plurality of sensors 208 every 30 seconds. Sensors 208 may include time-sparse measurements (long duration between sampling points in time), consistent with possibly low-bandwidth transmission methods in the surface mount. Long-period internal waves within maritime region 201 are a propagating disturbance, perturbing various of the maritime model parameters with spatial and temporal dependency defined by the wavefield. This perturbative effect can be detected using one or more of plurality of sensors 208. Additionally, measurements of travel-time variance in an acoustic monitoring network either associated with or separate from the global PNT system can be used to obtain updated changes to the Garrett-Munk spectrum representation, including geographic variability. Such knowledge can be used to improve the accuracy of statistical modeling of the effects of short-period internal waves on acoustic waves generated by the positioning system.

According to an embodiment, maritime data 212 is received by a processing station 214. In some embodiments, maritime data 212 is first transmitted from water surface mount 204 to a satellite, or between a network of satellites, and then ultimately transmitted from one of the satellites to processing station 214. Processing station 214 may be located on land or on a ship. Processing station 214 may include any number of RF components (receivers, transmitters, and/or transceivers) configured to receive maritime data 212. Processing station 214 also includes any number of processing devices designed to collect maritime data 212 over time and derive model update parameters to be made to a maritime model of maritime region 201. The model update parameters are used to account for the effects of long-period and/or short-period internal waves within maritime region 201, according to some embodiments.

In some embodiments, model update data 216 is received by water surface mount 106 of signal beacon 104a. In some embodiments, model update data 216 is first transmitted from processing station 214 to a satellite, or between networked satellites, and then ultimately transmitted from one of the satellites to signal beacon 104a. Any signal beacon within maritime region 201 could be used to receive model update data 216.

Signal beacon 104a may be designed to generate an acoustic signal to transmit through maritime region 201, where the acoustic signal has encoded data associated with the model update parameters in model update data 216. Accordingly, transducer system 110 may generate acoustic model update data 218 that is received by underwater vehicle 112. In some embodiments, the same acoustic signal generated by transducer system 110 that is used for geolocating underwater vehicle 112 also includes the model update parameters encoded on the signal. In some other embodiments, separate and distinct acoustic signals are generated by transducer system 110 for geolocating underwater vehicle 112 and transmitting model update parameters. Underwater vehicle 112 receives acoustic model update data 218 and updates a stored maritime model using the received model update data 218. The updated maritime model may account for the effects of long-period and/or short period internal waves to provide a more accurate geolocation determination. In one embodiment, the maritime model data may be derived from means entirely independent of the apparatus of the measurement system, and rebroadcast acoustically. This data may, for example, provide the information needed to regionally or globally update the reference maritime model in a dynamically consistent manner.

With regards to the long-period internal waves, the model update parameters may be derived using a suitable inverse theory that estimates coefficients of a physics-based representation of the internal wave field by fitting the model to data measurements whose values and variability encode the spatio-temporal influence of the internal waves on the corresponding physical quantity. One example type of data suitable for this purpose is thermistor recordings acquired on a vertical array in the maritime region. The horizontal propagation component of the long-period internal waves is represented with a Fourier synthesis. According to some embodiments, in order to fit a propagating wave field to such data and distinguish the perturbations due to internal wave motion from other sources of variability, it is preferred to have sufficient depth span of sensors on the vertical array, sufficient spatial sampling density (or distribution) on the vertical array, and a sufficient spatial distribution of such arrays in or near the maritime region(s) of interest. When attached to a vertically stationary array, the temperature measurements reveal the changing temperature of the local environment caused by the internal wave adiabatic displacement of "fluid parcels" in the maritime column. The appropriate modal basis set corresponds to the orthogonal internal wave modes. The modes can be computed for a given vertical stratification of the maritime model parameters, as defined by the onboard maritime reference model. The mode eigenfunctions and eigenfrequencies can be pre-computed and stored at the beginning of a mission. These mode properties can be recomputed onboard the underwater vehicle if a reference maritime model update becomes available. The coefficients representing the global propagating field can be fit over the modes using observed perturbations to the temperature field as mentioned above, or to perturbations in other reference quantities (e.g., salinity, pressure), or to the vertical velocity field, or in any combination of these data sources as obtained from a distribution of vertical line arrays fitted with the corresponding sensor types. Once derived in a global processing center, the model update parameters may be transmitted to the acoustic source system as model update data 216, and, in turn, broadcast acoustically to the undersea vehicle(s).

Accounting for the effects of short-period, short-wavelength internal waves involves a stochastic approach since it is not feasible from a practical stand-point to acquire the measurements over a basin-scale that would be necessary for a deterministic, phase-coherent estimation procedure. Solving for the effect of the short-period internal waves may involve solving a classic sound-speed tomography problem based on measuring times-of-flight $\tau_{ij}$ between a set of transmitters at positions $x_i^T$ and receivers $x_j^R$. It is assumed that the sound speed profile $c(x)$ varies sufficiently smoothly that geometrical optics applies, and hence that $\tau_{ij}$ may be determined by tracing the ray (or rays) connecting the two positions. The underlying formalism may be represented as $$\tau_{ij} = \int_{\Gamma_{ij}} \frac{|dx|}{c(x)} \tag{1}$$

in which the line integral is along the trajectory $\Gamma_{ij}$ defined by the ray tracing equations. In the presence of multipath, Equation (1) can be generalized to include several different paths $\Gamma^{(n)}_{ij}$, n=1, 2, 3, . . . , connecting the two points, with different flight times $\tau^{(n)}_{ij}$. If one uses a representative grid of values $c \equiv \{c_l = c(x_l), l=1, \ldots, N_G\}$, along with an appropriate interpolation scheme, the forward problem produces a function $$\tau_{ij} = \tau_{ij}(c). \tag{2}$$

A given ray path will produce dependency only on values $c_l$ whose grid element is intersected by the ray. The tomography problem consists of inverting Equation 2 for c. The accuracy and stability of the inversion will be dependent on how densely the ray paths $\Gamma_{ij}$ cover the exploration volume. A high-resolution inversion will likely require that the number of paths be comparable to $N_G$, depending on the degree of valid prior smoothness constraints one may apply.

This problem becomes more difficult if $c(x)$ has fine scale variation due to, for example, short-period internal wave effects that may only be effectively characterized statistically. The travel times $\tau_{ij}$ and paths $\Gamma_{ij}$ will then also have a stochastic element. The object then is to pose a tomographic problem for the statistics of c (e.g., mean and variance) rather than the precise deterministic values. The advantage is that these statistical parameters may be assumed to vary slowly in space, and hence may be characterized by a much coarser grid.

Since small-scale variations (comparable to the short-period wavelength) are involved, scattering phenomena, not captured by direct ray tracing, may occur. According to an embodiment, a modal approach is used that enables a much more accurate treatment that accounts for vertical structure within a vertical eigenmode treatment, and the horizontal structure within a 2D modal ray tracing formalism. The sound speed may be written in the form $$c(x) = c_0(x) + \delta c(x), \tag{3}$$

in which a separation of scales is assumed in which $|\delta c| \ll c_0$ is small, and also varies on scales shorter than $c_0$. Even more specifically, based on the particular maritime region, an assumption can be made that $c_0(x) = c_0(\rho, z)$ is mainly a function of height z (with 1-2% variation on 100 m scales), varying much more slowly with horizontal coordinate $\rho$ (with variation on multi-km scales or larger). The fluctuation $\delta c/c$ is small compared to this $O(10^{-2})$ variation, so that it provides only a perturbative correction to the sound channel propagation. With geometrical optics, time-of-flight of a propagating acoustic signal through the maritime region may be represented as $$\tau = \int_\Gamma \frac{|dx|}{c} = (\tau_0 + \delta\tau_1)\{1 + O[(\delta c/c_0)^2]\} \tag{4}$$

where $$\tau_0 = \int_{\Gamma_0} \frac{|dx|}{c_0}, \delta\tau_1 = -\int_{\Gamma_0} |dx| \frac{\delta c}{c_0^2} \tag{5}$$

in which $\Gamma$ is the exact path generated by c, and $\Gamma_0$ is the approximate path generated by $c_0$. Fermat's principle guarantees that ray path perturbations due to $\delta c$ lead only to second order corrections to the travel time, allowing one to use $\delta_0$ to compute the linear correction $\delta\tau_l$. In terms of physical measurement, $\delta c$ fluctuates (on, for example, 10 min time scales), with mean zero, $\langle \delta c \rangle = 0$, while $c_0 = \langle c \rangle$ may be viewed as fixed (e.g., on hourly time scales).

According to an embodiment, the sound-speed tomography goal is to determine $c_0(x)$, which therefore follows by tracking the mean flight times $$\tau_{0,ij} \equiv \langle \tau_{ij} \rangle = \int_{\Gamma_{0,ij}} \frac{|dx|}{c_0}, \tag{6}$$

having $O[(\delta c/c_0)^2]$ errors. Since instantaneous values will contain $O(\delta c/c_0)$ errors, the history of each $\tau$ may be tracked, forming a distribution $P_{ij}(\tau)$ (which itself may vary only on hourly timescales). In one example, for long paths sampling many independent sound-speed fluctuations, $P_{ij}$ will be Gaussian, and its mean and variance can be tracked, e.g., using a Kalman filter.

Included in the $\delta\tau_2 \equiv O[(\delta c/c_0)^2]$ corrections is a nonzero mean $\langle \delta\tau_2 \rangle$ which therefore produces a small bias on the mean time-of-flight, depending on the sound-speed fluctuation spectrum. For example, using distance d=1500 km, wavelength $\lambda$=1.5 km, $\delta c/c = 10^{-3}$, it can be determined that $\delta\tau_1 \sim (\sqrt{d\lambda}/c)(\delta c/c) = 1$ ms (a result of $1/\sqrt{N}$ self-averaging over N=d/$\lambda$ wavelengths), $\delta\tau_2 \sim (d/c)(\delta c/c)^2 = 1$ ms. It follows that standard deviation and bias are comparable on such scales. For high accuracy geolocation over large ranges, computing and removing this bias caused by the short-period internal waves is desired. In order to do this, the fast-time fluctuation spectrum is determined as discussed below—this is the internal wave statistical tomography problem.

The travel time variance of propagating acoustic signals in the presence of the short period internal waves takes the form $$\langle \delta\tau_1^2 \rangle = \int_{\Gamma_0} \frac{|dx|}{c_0(x)^2} \int_{\Gamma_0} \frac{|dx'|}{c_0(x')^2} C(x, x') \tag{7}$$

with correlation function $$c(x,x') \equiv \langle \delta c(x) \delta c(x') \rangle \tag{8}$$

The variance is already $O[(\delta c/c_0)^2]$. Under the channel assumptions above (e.g., for a given maritime environment), to leading order, with $O(10^{-2})$ corrections, $c_0(x)$ may be replaced by a uniform representative value, for example, $\bar{c}_0=1500$ m/s. Equation (7) may then be approximated by $$\langle \delta\tau_1^2 \rangle = \frac{1}{\bar{c}_0^2} \int_{\Gamma_0} |dx| C_{\Gamma_0}(x), \tag{9}$$

where $C_{\Gamma_0}(x)$ is defined as $$C_{\Gamma_0}(x) = \frac{1}{\bar{c}_0^2} \int_{\Gamma_0} |dx'| C(x, x'). \tag{10}$$

The integral in Equation (10) may be along the ray path $\Gamma_0$ passing through x. More explicitly, $$\langle \delta\tau_1^2 \rangle = \frac{1}{\bar{c}_0^2} \int dl\, C_{\Gamma_0}[x(l)] \tag{11}$$

$$C_{\Gamma_0}[x(l)] = \frac{1}{\bar{c}_0^2} \int dl'\, C[x(l), x(l')]$$

where l represents parameterization with respect to arc length, $dl=|dx|=cdt$. Since $\delta c$ represents fluctuations due to short-period wavelength (e.g., having a wavelength of a few km) internal waves, it is generally found that $C(x, x')$ also has a range of only a few km. The ratio $$L_p(x) = \frac{C_{\Gamma_0}(x)}{C(x, x)/\bar{c}_0^2} \tag{12}$$

represents an along-ray correlation length, and is also found to be a few km. According to an embodiment, $C_{\Gamma_0}[x(l)]$ will be a strong function of z(l), on 100 m scales, due to relatively strong variation of all quantities with height z within the given maritime region, as well as the angle of the ray at the point x(l) which determines how rapidly the acoustic signal is traversing through the maritime region. Based on Equations 9-12, an estimate $\langle \delta\tau_1 \rangle \sim (L_p d/c_0^2)(\delta c/c_0)2$ can be obtained. The estimate is consistent with Equation (6) using the more carefully defined length $L_p$ to replace $\lambda$.

According to an embodiment, $\delta c$ originates from vertical fluid displacement due to an internal wave field represented by $\zeta(x)$, $$\delta c(x) = (\partial_z c_0)_p(x)\zeta(x), \tag{13}$$

where $(\partial_z c_0)_p$ denotes a potential sound speed derivative, accounting for the adiabatic pressure and temperature change with fluid parcel motion. Substituting Equation (13) into Equation (8) obtains $$C(x,x') = (\partial_z c_0)_p(x)(\partial_z c_0)_p(x') R(x,x')$$

$$R(x,x') = \to \zeta(x)\zeta(x')\rangle. \tag{14}$$

Locally, on scales smaller than the horizontal variation of $c_0$, the internal wave field may be expressed in the form of a modal sum $$\zeta(x, t) = \sum_j \int \frac{d^2q}{(2\pi)^2} \zeta_j(q, z) e^{i[q\cdot\rho - \omega_j(q)t]} \tag{15}$$

in which the vertical mode shapes $\zeta_j(q; z)$, with frequency eigenvalue $\omega_j(q)$, are governed by the Brunt-Väisälä frequency profile $N(z)=\sqrt{(g/\rho_p)|\partial_z\rho_p|}$, where $\rho_p$ is the potential density. The index j is due to the discrete set of $\zeta_j$ consistent with the surface and bottom boundary conditions of the maritime region. Defining the internal wave spectrum $\hat{S}_j(q; z, z')$ by $$\langle \zeta_j(q,z)\zeta_k(q',z')\rangle = \delta_{jk}\delta(q+q')\hat{S}_j(q;z,z'), \tag{16}$$

the internal wave correlation function R takes the form $$R(x, x') = \sum_j \int \frac{d^2q}{(2\pi)^2} e^{iq\cdot(\rho-\rho')} \hat{S}_j(q; z, z'). \tag{17}$$

In $S_j$ and R, a slow dependence on the center coordinate $\bar{\rho}=(\rho+\rho')/2$ has been suppressed from the notation. The dependence on the difference coordinate is much stronger, with R vanishing with increasing $|\rho-\rho'|$ on the scale of a few km.

The short period internal wave tomography problem may be represented in terms of Equations (9) or (11). By tracking the variance $\langle \delta\tau_{ij}^2 \rangle$ for each transmitter-receiver pair, an inverse problem to characterize the internal wave correlation function R may be produced. Given that the data represents a sparse set of line integrals through any given region, characterization may rely on prior knowledge about its functional form, with a minimal set of fitting parameters. Accurate model forms for the spectrum have been developed that rely on accurate knowledge of $N(z; \bar{\rho})$, but beyond this involve an overall amplitude parameter $\zeta_0(\bar{\rho})$ and a width parameter $j_*(\bar{\rho})$. These parameters may be fixed at universal values, such as, for example, $\zeta_0=7.5$ m and $j_*=3$. Under the assumption that N is obtained through a separate measurement campaign, the inverse problem may be solved for these two parameters (or perhaps a few more, if required for higher accuracy representation, e.g., over a broader spectral range) to determine the effect of the short-period internal waves on the propagation of an acoustic signal through the maritime region.

Although only one signal beacon 104a and one measurement apparatus 202 are illustrated in FIG. 2, any number of signal beacons and measurement apparatuses can be used in a given maritime region 201 to collect maritime data and transmit the data ultimately to underwater vehicle 112. In some examples, a plurality of measurement apparatuses 202 are placed about 10 meters apart within maritime 201 region. Furthermore, in some embodiments, one or more of plurality of sensors 208 could be disposed along the cable length of different signal beacons in a given maritime region. In such situations, the signal beacons can serve two functions: (1) to provide acoustic signals for geolocating underwater vehicle 112, and (2) to measure maritime data using plurality of sensors 208. The measured maritime data may then be used to derive model update parameters that are acoustically transmitted to underwater vehicle 112. Deriving the model update parameters may be performed by processing station 214, or by one or more processing devices on a given signal beacon. Alternatively, a separate maritime observing network can be used to record acoustic waves generated by acoustic sources the same as those used in the positioning system, or apart from the positioning system. The acoustic data collected in such a way can be processed for statistical characterization of short period, short-wavelength internal wave effects on acoustic travel times in a manner similar to that described above.

Transducer System

Figure 3:
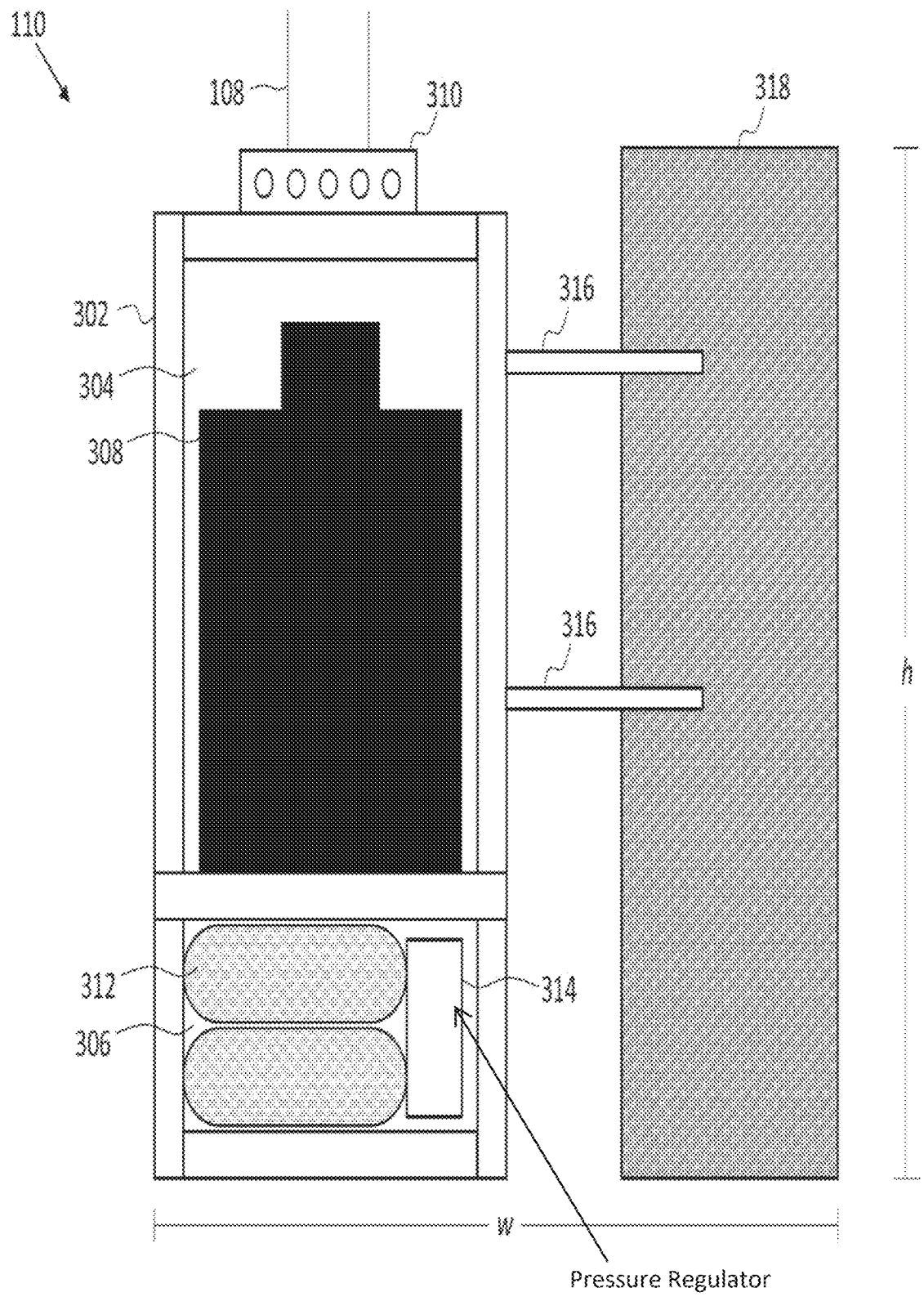
FIG. 3 illustrates an example electromechanical transducer, in accordance with some embodiments of the present disclosure.

FIG. 3 illustrates a more detailed view of transducer system 110, according to an embodiment. Transducer system 110 may include a housing 302 to protect the various elements of transducer system 110, and to act as a mechanical support member when lifting or lowering transducer system 110. Housing 302 may be fully enclosed or may include only frame members with the sides being open (e.g., a cage). Housing 302 may define a first chamber 304 and a second chamber 306. In some embodiments, transducer system 110 has a total height h between about 90 inches and about 100 inches, and a total width w between about 90 inches and about 100 inches.

In some embodiments, first chamber 304 includes an electromechanical transducer 308. Electromechanical transducer 308 may include a piezoelectric ceramic material, or a stack of piezoelectric ceramic materials, according to some embodiments. Examples of piezoelectric ceramic materials include barium titinate or lead zirconate titanate. Such materials produce a mechanical stress when an electric charge is applied and vice versa. In some embodiments, electromechanical transducer 308 includes one or more piezoelectric crystals such as quartz, Rochelle salt, or ammonium dihydrogen phosphate. In some embodiments, electromechanical transducer 308 includes one or more magnetostrictive materials that expand or contract in response to a magnetic field. In a more general sense, any number of transducer mechanisms can be used to implement transducer region 308. The transducer elements within first chamber 304 may include a Tonpilz style transducer, a flextensional transducer or a barrel stave transducer, to name a few examples. In general, any electromechanical transducer capable of producing acoustic waves between 10 Hz and 1000 Hz may be used.

When used for sonar, electromechanical transducer 308 vibrates due to the flexing of the piezoelectric materials that are mechanically coupled to a "shell" or "hull", and thereby produces mechanical waves through the surrounding water. The outer material of electromechanical transducer 308 may include a rigid metal casing, such as steel, along with an elastomeric material stretched over the metal casing.

Second chamber 306 may include a pressurized system having one or more pressurized tanks 312 and a pressure regulator 314. One or more pressurized tanks may include a pressurized gas, such as any inert gas like nitrogen. The gas may be pressurized up to about 6000 PSI. Pressure regulator 314 may be designed to control the pressure around or within electromechanical transducer 308 using the pressurized gas in tanks 312. For example, the pressure within electromechanical transducer 308 may be pressurized to an external-to-internal pressure differential between 30 psi and 150 psi. Since transducer system 110 is designed to be submerged deep under the water where the external pressure can become very high, it is advantageous to have the ability to control the internal pressure of the system to balance the pressure differential across electromechanical transducer 308.

Transducer system 110 includes one or more support rods 316 attached to a stabilizing fin 318, according to some embodiments. Stabilizing fin 318 may be used to counteract currents and other forces in the water that may cause the position of transducer system 110 to drift.

According to some embodiments, transducer system 110 includes a coupling plate 310 having one or more locations to couple with cable structure 108. Coupling plate 310 may provide locations to physically attach cable structure 108. Other portions of cable structure 108 may include electrical wires that extend down into either first chamber 304 or second chamber 306 to provide power and/or data transfer to the various components of transducer system 110.

Underwater Vehicle

Figure 4:
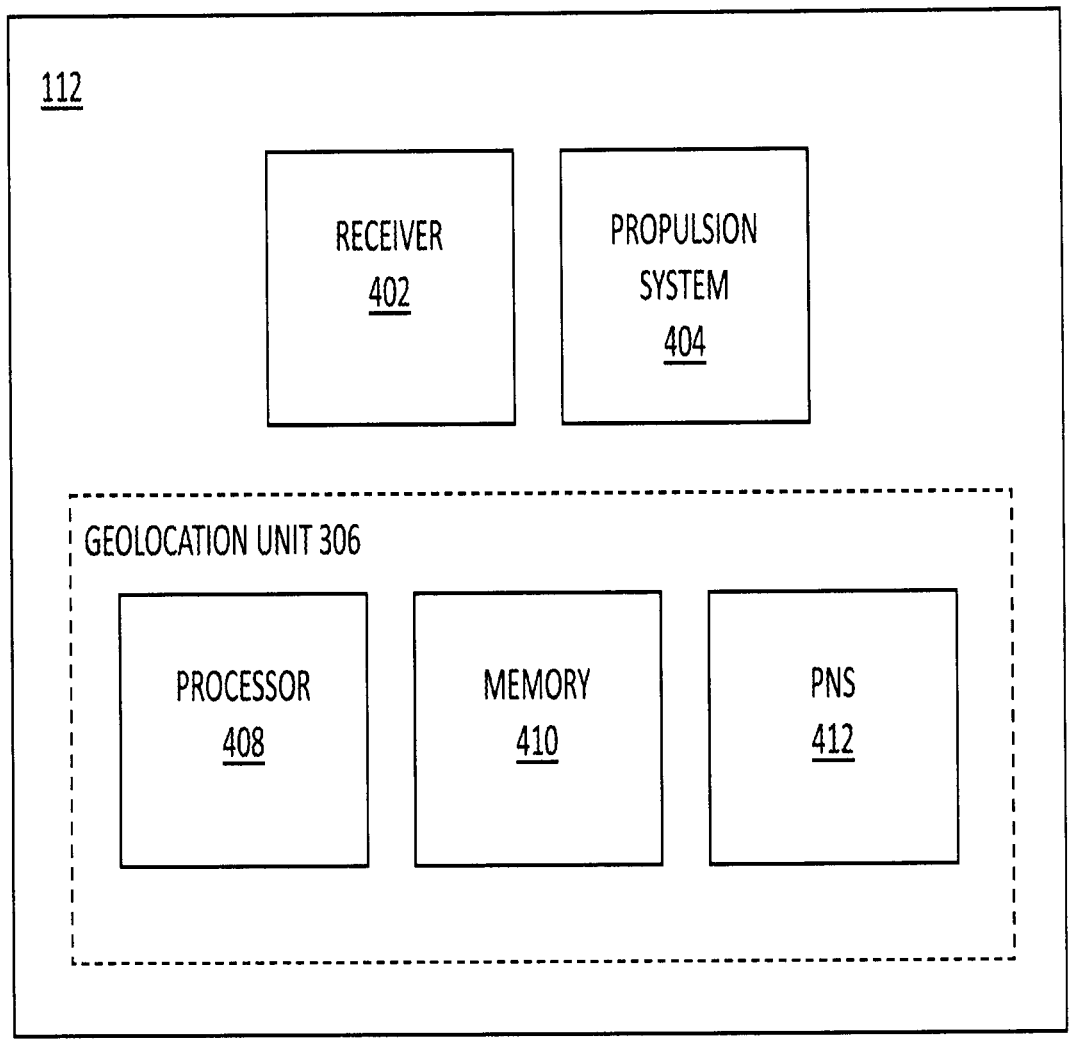
FIG. 4 illustrates components of an underwater vehicle, in accordance with some embodiments of the present disclosure.

FIG. 4 illustrates components present within underwater vehicle 112, according to some embodiments. Underwater vehicle 112 may include a receiver 402, a propulsion system 404, and a geolocation unit 406.

Receiver 402 may represent any one or more acoustic receivers (such as a sonar receiver) for transducing a received acoustic signal into an electrical signal. Receiver 402 may receive acoustic signals from one or more signal beacons underwater. According to some embodiments, receiver 402 may send the electrical signals corresponding to the received acoustic signals to geolocation unit 406 in order to estimate ranges to each of the one or more signal beacons. Such electrical signals may be the observed acoustic waveforms after propagation through the underwater medium between a signal beacon and receiver 402.

Propulsion system 404 may include any number of elements involved in moving underwater vehicle 112 once it is submerged. Accordingly, propulsion system 404 may include a motor, a fuel source, and a propeller or jet nozzle. In some examples, the motor can turn the propeller in the water to move underwater vehicle 112. In some other examples, the motor can activate a pump that forces water out of the jet nozzle to move underwater vehicle 112. In another embodiment the propulsion system may be a passive, buoyancy-based mechanism as used in some types of undersea gliders.

Geolocation unit 406 may include a processor 408, a memory 410, and a positional navigation system (PNS) 412. In some embodiments, PNS 412 is not included on underwater vehicle 112. For example, acoustic data may be recorded on the platform/vehicle, the data may be processed later by an off-board unit for the prior history trajectory. Further, that data may be accessed by physical recovery of the platform/vehicle. Alternatively, the data may be transmitted to satellite upon vehicle/platform surfacing (via Iridium, for example), or by RF link to a nearby, surface-based RF receiver. Processor 408 may represent one or more processing units that includes microcontrollers, microprocessors, application specific integrated circuits (ASICs), and field programmable gate arrays (FPGAs). According to some embodiments, processor 408 determines a geolocation of underwater vehicle 112 based on acoustic signals received at receiver 402 and a maritime model stored in memory 410. According to some embodiments, one or more of the parameters of the stored maritime model may be used to model the effects of long-period and/or short period internal waves, and such parameters may be updated using model update data provided from underwater measuring environment 200, or from a separate maritime observing network that generates the requisite data and which is then processed using the algorithms described herein.

Memory 410 may represent one or more memory devices that can be any type of memory. The memory devices can be one or more of DDR-SDRAM, FLASH, or hard drives to name a few examples. The maritime model may be pre-loaded into memory 410 before underwater vehicle is submerged. In some embodiments, the maritime model includes a plurality of parameters associated with various aspects of the marine environment, such as a reference model comprised of temperature, salinity, meridional and zonal velocities from the general circulation, and sea surface height (SSH). Additional parameters may include those supporting predictive models for tidal currents. Maritime model perturbations due to dynamical effects such as short period or long period internal waves, are accommodated via other means as described below. The maritime model may receive updates to one or more of these parameters via acoustic signals received by receiver 402 of underwater vehicle 112. For example, parameters used to remove the bias effect of short-period, short-wavelength internal waves may be updated on a periodic basis e.g., daily or weekly. Data pertinent for acoustic correction due to long-period, long-wavelength internal wave effects is likely transmitted on a more frequent basis e.g., hourly, every 6 hours, every 12 hours, etc. Other parameters of the maritime model may be viewed as fixed relative to perturbations induced by dynamical phenomena such as internal waves. In some embodiments, these fixed parameters are those that define the maritime reference model i.e., temperature, salinity, meridional and zonal velocity components of the general circulation, and sea surface height. These more slowly varying (secular) parameters may be updated via a means consistent with acoustic bandwidth constraints on undersea communications, using for example, a perturbative treatment employing a compact set of transmitted parameters. Further, the update frequency for adjustments to the maritime reference model may be on the order of once a day, or once a week, or once a month, i.e., less frequently than that required for the internal waves due to the slower dynamics.

According to some embodiments, processor 408 determines a predicted acoustic signal that would be received at a hypothesized range from a given signal beacon using the maritime model and compares (using a suitable metric) the predicted acoustic signal to an actual acoustic signal received from the given signal beacon. The difference between the predicted signal and actual received signal can be used to drive a new hypothesis for the range distance estimation in an optimization process, and the model is then used to compute a new predicted signal. This process may be iterated until the predicted signal and received signal are sufficiently similar in accordance with a tolerance dependent on the selected metric. According to some embodiments, the corresponding final hypothesis constitutes the estimated range. Alternatively, this process is repeated, but with a plurality of signal beacons, in which the vehicle/platform position is the common unknown model parameter. The optimal position estimate is the one that minimizes a misfit measure computed over all the received waveforms from each of the signal beacons. In one embodiment the unknown model parameters are the vehicle/platform position and velocity (or track).

PNS 412 may be included as part of geolocation unit 406 to provide additional data input for determining and/or refining the position of underwater vehicle 112. PNS 412 may include one or more inertial sensors that track movement of underwater vehicle 112, and thus can store a "route" that underwater vehicle 112 has taken over a given time period. Inertial sensors of realistic expense for non-submarine vehicles will develop large errors within minutes (or even seconds) from an initial reference state. Their utility for a PNS therefore relies on periodic (or punctuated) reinitialization of the vehicle position estimate (e.g., via acoustic means), and the inertial measurement data can then be used to provide continuous input for navigation intermediate to acoustic fixes of position estimation. There are other measurement modalities that may complement the inertial sensors. One such modality is magnetic field measurement, which may constrain bearing. Another measurement modality is the Doppler Velocity Log (DVL), which constrains relative velocity of the vehicle/platform. Continuous measurements from the inertial sensors, magnetic sensors, and DVL sensors can be used to inform a track estimator e.g., such as a Kalman Filter for continuous kinematic estimation and updating.

Methodology

Figure 5:
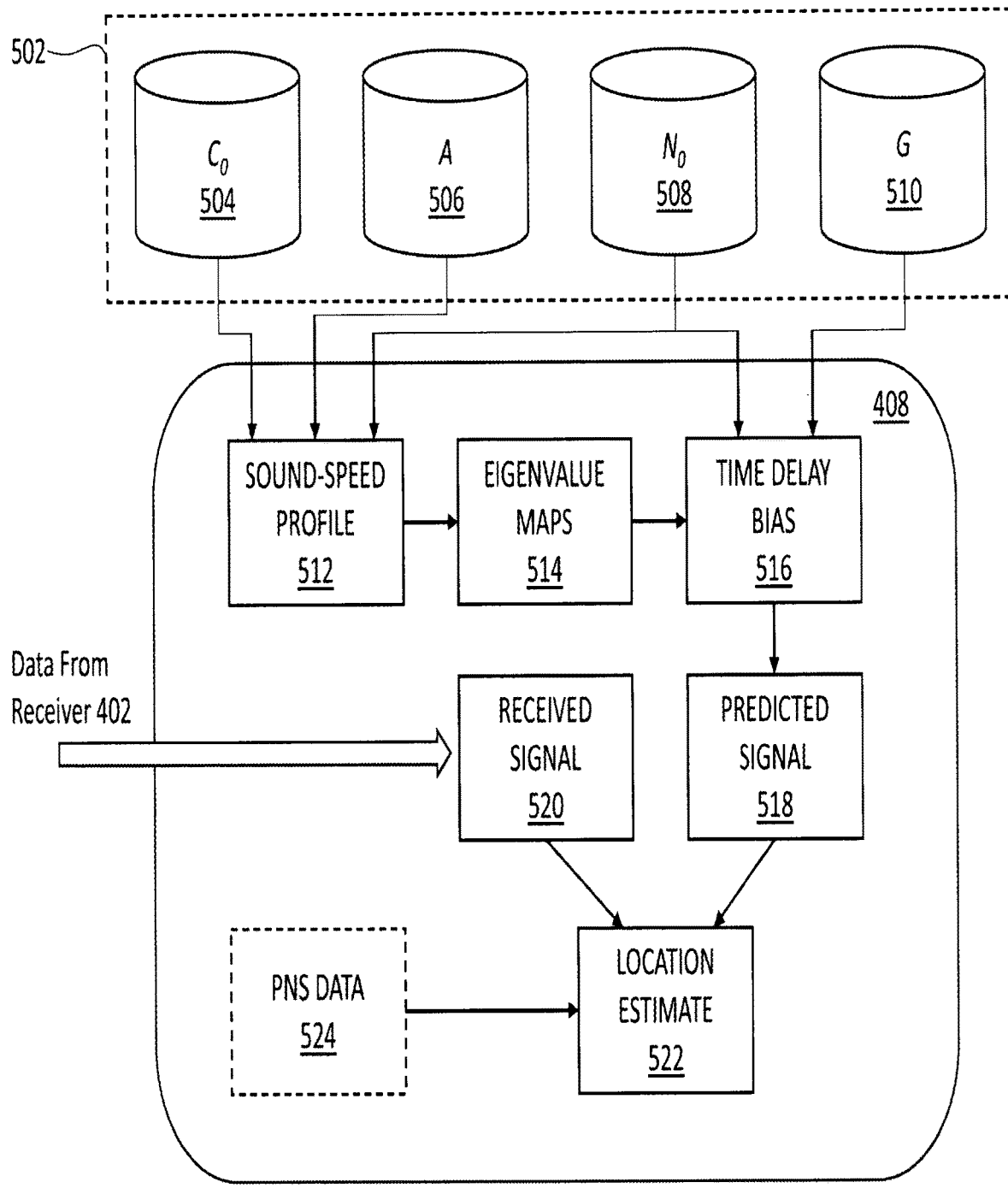
FIG. 5 illustrates operations of an example processing device on the underwater vehicle, such as the one shown in FIG. 4, in accordance with an embodiment of the present disclosure.

FIG. 5 illustrates example operations performed by processor 408 to determine a geolocation of underwater vehicle 112 using parameters from a maritime model 502, according to an embodiment. Maritime model 502 may be represented by a plurality of data stores that store various parameters used to define certain aspects of the marine environment. The plurality of data stores may be on a same memory device or spread across multiple memory devices. As noted above, according to some embodiments, one or more of the parameters of the stored maritime model 502 are determined, at least in part, by measuring various maritime parameters within an underwater measuring environment 200.

A first data store 504 may include data associated with a base (or reference) basin-scale sound-speed map ($C_0$) of the surrounding maritime environment. The base sound-speed map $C_0$ may be deduced from maritime reference parameters such as water temperature, salinity, and pressure (or alternatively, water temperature, salinity, and density). Several of these variables may be dependent on one another according to an equation of state appropriate to the maritime region. The base sound-speed map $C_0$ may be stored in first data store 504 before underwater vehicle 112 is submerged. A second data store 506 may include parameters associated with long period, long wavelength Fourier amplitudes (A) that comprise the propagating internal wave spectrum in the maritime region encompassing the signal beacon(s) and the target receiver(s). As the internal wave field is dynamic, and essentially unknowable at distant times in the future, the amplitude data may be acoustically broadcast to the undersea vehicle/platform. The Fourier amplitude data (A) may be used by processor 408 to determine the effect of long-period internal waves on the maritime model and thereby on predicted waveforms. In the above terminology, long period waves are internal waves having a wavelength between ~100 km and 1000 km (or greater). The Fourier amplitude data (A) stored in second data store 506 may be transmitted acoustically to underwater vehicle 112 and updated periodically. A third data store 508 may include parameters associated with a buoyancy frequency map ($N_0$). In some embodiments, the buoyancy frequency defines the Brunt-Väisälä frequency profile shown below in Equation (18), $$N(z) = \sqrt{-g \partial_z \rho / \rho_0} \qquad (18)$$

which may be used to determine the effects of both long-period internal waves and short-period internal waves. The form of N(z) also determines the internal wave dispersion relation and vertical mode profiles. N(z) will vary with the geographic position in the maritime model and may be computed onboard using the maritime model. Additionally, N(z) may be pre-computed for the maritime model i.e., prior to loading it onto the vehicle/platform. Short period, small wavelength waves are another component of the internal wave spectrum. In this taxonomy they are internal waves having a wavelength between 1 m and 10 km. The Brunt-Väisälä frequency profile may be computed by processor 408 and stored in third data store 508. A fourth data store 510 may include parameters associated with a Garrett-Munk model (G) having geographic heterogeneity used by processor 408 to statistically determine the effects of short-period internal waves. Both long-period internal waves and short-period internal waves may delay the arrival of an acoustic wave by a determined time bias. The Garrett-Munk model data (G) stored in fourth data store 510 may be transmitted acoustically to underwater vehicle 112 and updated periodically.

According to an embodiment, processor 408 generates a sound-speed profile 512 using various parameters from data stores 504, 506, and 508. Contributions from data stores 504, 506, and 508 define the sound speed profile due to the base sound-speed map plus the added dynamic effect on sound speed due to long-period, long-wavelength internal waves. The time-delay bias due to short-period internal waves follows from a fluctuation spectrum of sound wave perturbations and may be computed for a given acoustic arrival time that is experimentally observed, and then corrected with an appropriate theory. In some embodiments, the generation of sound-speed profile 512 involves the summation of various sound speed perturbations in conjunction with the base sound-speed map $C_0$. In one example, thermodynamic effects and sea surface height effects induced by tides are added to the sound-speed map $C_0$. In contrast to long period internal waves as represented by the coefficients A, the tidal effect can be computed with a pre-loaded, parameterized model.

A large fraction of the variance in many oceanographic variables is due to tides. Satellite and in situ data may be acquired to estimate coefficients of empirical and physics-based models. Accurate maps of tidal currents or elevations are useful for various marine applications, and acoustic geolocation is no exception. Tidal effects can have significant effects on travel time arrivals, particularly over long propagation distances. These effects can change the boundary conditions for acoustic propagation e.g., due to change in sea surface height, cause advection of acoustic wave fronts due to the tidal velocity field and cause thermodynamic changes as well (mainly due to the baroclinic component which vertically displaces the fluid). These effects can be modeled with physics-based tidal models with coefficients fit to the available data sources. The tidally induced changes in the maritime model can be used to compute the corresponding expected perturbations in the observed acoustic field (e.g., travel times or full waveforms), thereby yielding a tide-corrected waveform for comparison to data. Alternatively, the acoustic perturbation can be added to the synthetic, predicted data, prior to comparison to the measurement data.

Long-period internal waves are directly affected by tides due to the altered boundary conditions and perturbed profile of internal ocean parameters. Additionally, the spectrum of internal waves can also be affected by anomalous events such as storms, and the distribution of energy in these wave modes is further altered by multiple processes including nonlinear modal coupling. Long-period waves may be viewed as being "deterministic" since, once generated, they can be estimated from a global observation network and their propagation parameters (e.g., excitation coefficients referenced to an appropriate basis set) can be transmitted to underwater vehicle 112 for on-board correction of measured travel times. Long-period internal waves affect the base sound speed map $c_0$ in the form $$c(r,z,t)=c_0(r,z,t)+\zeta(r,z,t)\partial_z c_p \tag{19}$$

where c(r, z, t) is the slowly varying background profile (e.g., computed from a general circulation model, but with internal waves filtered out), $\partial_z c_p$ is an adiabatic derivative, and where $$\zeta(r,z,t) \approx \sum_{k,n} \hat{\zeta}_{k,n}(z) e^{i(k\cdot r - \omega_{k,n} t)} \tag{20}$$

is the wave amplitude, written here locally as a superposition of oscillating wave normal modes. Time-of-flight predictions may be obtained by tracing rays through this perturbed sound speed profile, and this provides a higher fidelity model for the geolocation inversion. This operation may be performed onboard the underwater vehicle.

Generally, the base sound speed map $c_0$ may be generated via a maritime state estimation using data assimilation. For example, an adjoint-based method may be used where a nonlinear forward model (denoted below by M) is specified and evolves in time a maritime state vector v according to equation (21):

$$v(t)-M[v(t-1)]=0 \tag{21}$$

where the state vector components are given by the temperature, salinity, meridional and zonal velocity components and the sea surface height and assigned according to a spatial grid.

For estimation, a least squares cost function $J_0$ characterizing the data misfit is defined as:

$$J_0 = \Sum_{t=1}^{t_f}[d(t)-E(t)v(t)]^T R^{-1}[d(t)-E(t)v(t)]^T \tag{22}$$

where d(t) are measurements of maritime properties and E(t) is a measurement model. An extended Lagrangian function J may be defined as:

$$J = J_0 - \Sum_{t=1}^{t_f} \mu^T(t)(v(t)-M[v(t-1)]) \tag{23}$$

Equations (22) and (23) together lead to a system of normal equations for maritime model state variables v(t) that combine measurement and dynamical constraints, according to some embodiments. The Lagrange multipliers μ(t) are the adjoint model state variables and provide the gradient of the cost function used to define initial conditions (ICs), boundary conditions (BCs), internal physical parameters, etc.

According to an embodiment, processor 408 computes 2D eigenvalue maps 514 for each acoustical propagation mode determined from sound-speed profile 512. These maps may be used to define, in turn, the geographic variation of phase and group velocities to provide accurate computation of propagating wavefields composed of these modes. Vertical eigenmodes may be calculated according to the vertical stratification defined by the reference maritime model and the detailed structure of these modes change according to the slowly varying horizontal inhomogeneity. In general, the acoustic field at a given location x may be defined as a superposition of horizontally propagating modes defined as:

$$\varphi(x,t) = \sum_{n=1}^{\infty} A_n e^{i[k_n(\omega)r - \omega t]} \cdot \phi_n(z) \tag{24}$$

The eigenvalue equation for vertical mode profiles is given by:

$$\left[\frac{d^2}{dz^2} + \frac{\omega^2}{c(z)^2}\right]\phi_n = \Lambda_n(\omega)\phi_n \tag{25}$$

$$\Lambda_n(\omega) = |k_n(\omega)|^2$$

The index n corresponds to a particular discrete launch angle, and also defines the number of zero-crossings of the mode in the vertical dimension. Index n=1 is the fundamental mode (at fixed frequency) with no zero-crossing. Index n=2 is the first overtone and has one zero-crossing, etc. In the presence of horizontal inhomogeneity, vertical modes can be defined locally by:

$$\varphi(x,t)=\Sigma_{n=1}^{\infty}A_n(r)e^{i[\phi_n(r)-\omega t]}\cdot\phi_n(z;r) \quad (26)$$

where the governing equation of the modes is given by:

$$\left[\frac{d^2}{dz^2}+\frac{w^2}{c(z;r)^2}\right]\phi_n(z;r)=\Lambda_n(\omega;r)\phi_n(z;r) \quad (27)$$

where now $\Lambda_n(w;r)$ and $\phi_n(z;r)$ have dependence on the horizontal coordinate r relative to the corresponding Equations (24) and (25) provided above.

According to an embodiment, horizontal ray tracing based on the eigenvalue modes provided above in Equation (27) are generated using Hamiltonian particle dynamics where:

$$H_n(r,p)=\frac{1}{2}\left[p^2+\Lambda_n(r)\right] \quad (28)$$

$$\frac{dr(s)}{ds}=\frac{\partial H_n}{\partial p}=p(s) \quad (29)$$

$$\frac{dp(s)}{ds}=-\frac{\partial H_n}{\partial r}=\frac{1}{2}\nabla\Lambda_n(r(s)) \quad (30)$$

Equation (30) shows how gradients in $\Lambda_n$ lead to ray refraction. The phase progression in propagating from transmitter location $r_T$ to receiver location $r_R$ is given as $$\phi(r_R,r_T)=\int_{r_T}^{r_R}p(s)\cdot dr(s)=\int_{r_T}^{r_R}\Lambda_n(r(s))ds \quad (31)$$

Equation (31) follows from the relation $$\nabla\phi(s)=p(s) \quad (32)$$

The total modal group velocity determines the time-of-flight of the acoustic wave as follows:

$$T_n(r_R,r_T)=\int_{r_T}^{r_R}\frac{|dr(s)|}{|v_{g,n}(s)|}=\int_{r_T}^{r_R}\frac{2p(s)}{\partial_\omega\Lambda_n(r(s))} \quad (33)$$

Given the result in Equation (33), the maritime acoustic propagation model reduces to an interpolated grid of $\Lambda_n(\omega_0;r)$ for the first few dozen modes, evaluated at the signal center frequency $\omega_0$. According to an embodiment, processor 408 applies a time delay bias 516 to account for the time delay bias induced by the short-period, short-wavelength component of the ocean internal wave spectrum. The effects of short-period internal waves can be treated stochastically, by an appropriate computation whose input quantities include using either the wave spectrum derived from the Garrett-Munk model data (G), or geographic perturbation of G estimated by other means and communicated to the underwater vehicle through acoustic transmission e.g., on a once per day basis, and the buoyancy frequency map ($N_0$). The computation yields a time of arrival (ToA) correction (e.g., a determined delay in the arrival times of the acoustic signal caused by the short-period internal waves) which can be applied to observations. According to an embodiment, once the appropriate time delay has been determined, processor 408 can generate a predicted signal 518 that would be received from a signal beacon at a given estimated range separation. Other effects such as those due to long-period internal waves, tides, and ocean structure in the ocean reference model itself can be accounted for to achieve more accurate geolocation. The effect of long-period internal waves is accounted for using inputs A from 506. The effect of tides are readily incorporated into the reference model $C_0$ using the physics-based, parameterized tide model and knowledge of the date and time. In some embodiments, the prediction may only be a ToA predication for the signal received from the signal beacon.

Processor 408 also receives transduced acoustic data from receiver 402 corresponding to an acoustic pulse or continuous waveform transmitted from a signal beacon. The received signal 520 may include a mean average of arrival times for identifiable arrival pulses collected by receiver 402 over a period of time or it may include average variance of such arrivals. Processor 408 compares predicted signal 518 (or a predicted ToA for the signal) and received signal 520 (or the actual ToA for the received signal) to generate range separation estimates and a location estimate 522 for underwater vehicle 112. When using data from a single signal beacon, location estimate 522 provides a distance (or range) to the single signal beacon, but not an exact location due to ambiguity when using only the single source. However, by collecting acoustic signals received from a plurality of signal beacons and comparing the received signals to predicted signals from each of the plurality of signal beacons, a well-posed constraint on the geographic location of the undersea vehicle 112 can be determined.

In some embodiments, PNS data 524 collected from PNS 412 is also used by processor 408 when determining location estimate 522. For example, PNS data 524 may be used to refine location estimate 522 determined from the comparison between predicted signal 518 and received signal 520. In some embodiments, PNS data 524 may be jointly processed with non-PNS data in a "tightly-coupled" framework for joint estimation over PNS measurements and models with acoustics-based measurements and models for optimal geolocation (and/or kinematic estimation), consisting of the position/kinematic model most consistent with all of the available data to within the measurement noise of the various data types. Such an estimate is the Bayesian model estimate as this estimate not only maximizes the data likelihood over all the measurement types, but also admits prior information such as prior probability models on the expected distribution of the unknown model parameters.

Figure 6:
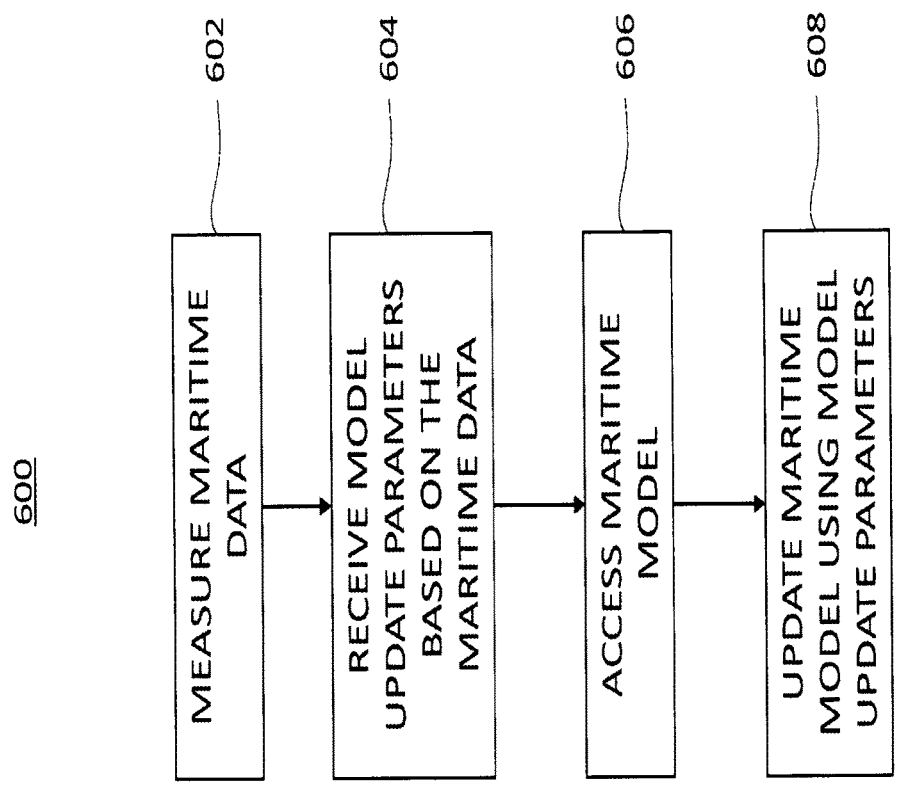
FIG. 6 illustrates a method of updating a maritime model to account for the effects of short period and/or long period internal waves, in accordance with some embodiments of the present disclosure.

FIG. 6 illustrates an example method 600 for updating a maritime model based on maritime data measurements to account for the effect of long-period and/or short period internal waves, in accordance with certain embodiments of the present disclosure. As can be seen, the example method includes a number of phases and sub-processes, the sequence of which may vary from one embodiment to another. However, when considered in the aggregate, these phases and sub-processes form a process for updating the maritime model. These embodiments can be implemented, for example using various ones of the systems illustrated in FIGS. 2 and 5, as described herein. However other system architectures can be used in other embodiments, as will be apparent in light of this disclosure. To this end, the correlation of the various functions shown in FIG. 6 to the specific components illustrated in the other figures is not intended to imply any structural and/or use limitations. Rather, other embodiments may include, for example, varying degrees of integration wherein multiple functionalities are effectively performed by one system. For example, in an alternative embodiment a single module having decoupled sub-modules can be used to perform all of the functions of method 600. Thus, other embodiments may have fewer or more modules and/or sub-modules depending on the granularity of implementation. In still other embodiments, the methodology depicted can be implemented as a computer program product including one or more non-transitory machine-readable mediums that when executed by one or more processors cause the methodology to be carried out. Numerous variations and alternative configurations will be apparent in light of this disclosure.

Method 600 begins at operation 602 where maritime data is measured using a plurality of sensors disposed within a maritime region, according to an embodiment. The plurality of sensors may be arranged along a length of a cable that is vertically oriented in the water using a weight at the bottom of the cable to maintain its orientation. The types of sensors that may be included in the plurality of sensors include thermistors, salinity meters, pressure sensors, acoustic receivers, and velocimeters, to name a few examples. Accordingly, marine-based parameters that may be measured include temperature, salt content, pressure, and velocity, to name a few examples. The measured maritime data may be transmitted from the measurement apparatus to either a processing station on land or on sea, to a signal beacon, or directly to an underwater vehicle.

Method 600 continues with operation 604 where model update parameters based on the maritime data are received by a processing device. The processing device may be on-board an underwater vehicle, in which case the model update parameters are acoustically received. The model update parameters may be acoustically received from a signal beacon as illustrated in FIG. 2. In some embodiments, the model update parameters are first derived from the maritime data at a processing station on land or on a ship at sea. The model update parameters may include parameters that model the effect of long-period and/or short-period internal waves on a propagating acoustic signal.

Method 600 continues with operation 606 where a maritime model is accessed. The maritime model, or portions of the maritime model, may be stored in a memory, or across multiple memory devices, on-board an underwater vehicle. According to an embodiment, the accessed maritime model may be associated with a particular signal beacon (e.g., modeling the underwater environment around a signal beacon) or with a particular maritime region. In one example, this model corresponds to an entire ocean basin. There may be different numerical, data-driven, and statistically based methods for generating maritime models. The localization method is not restricted to just one of these types of reference models. Any number of maritime models may be generated, stored and/or accessed where each maritime model is associated with a corresponding signal beacon or maritime region. The underwater vehicle may be deployed in differing maritime regions and models for each maritime region derived from distinct methods may be used in the localization processing. As discussed above, the maritime model may be defined by a collection of marine-based parameters and/or equations used to determine the effects that the maritime environment has on a propagating acoustic signal. At least some of the parameters of the maritime model are associated with the effects of long-period and/or short-period internal waves.

Method 600 proceeds to block 608, where the maritime model is updated or adjusted by, for example, changing one or more of the marine-based parameters associated with the model. According to some embodiments, the maritime model is updated using the received model update parameters in order to account for the effect of long-period and/or short-period internal waves, or to update the effect that long-period and/or short-period internal waves currently have in a given maritime region. The maritime model may be accessed and updated using one or more processing devices on-board the underwater vehicle. In this way, only model update parameters need to be transmitted to the underwater vehicle, reducing the signal bandwidth required in the acoustically transmitted signal. In some other embodiments, the model is accessed and updated using one or more processing devices in a processing station located on-land or at-sea. In such embodiments, the entire updated maritime model is then transmitted to the underwater vehicle. One or more processors on-board the underwater vehicle may use the updated maritime model when performing geolocation of the underwater vehicle as described above with reference to FIG. 5. In another embodiment the entire maritime model is updated, or just a given geographic region of the maritime model is updated using a compact information transmission from the signal beacon(s) and an onboard, physics-based perturbative treatment.

Computing Platform

Figure 7:
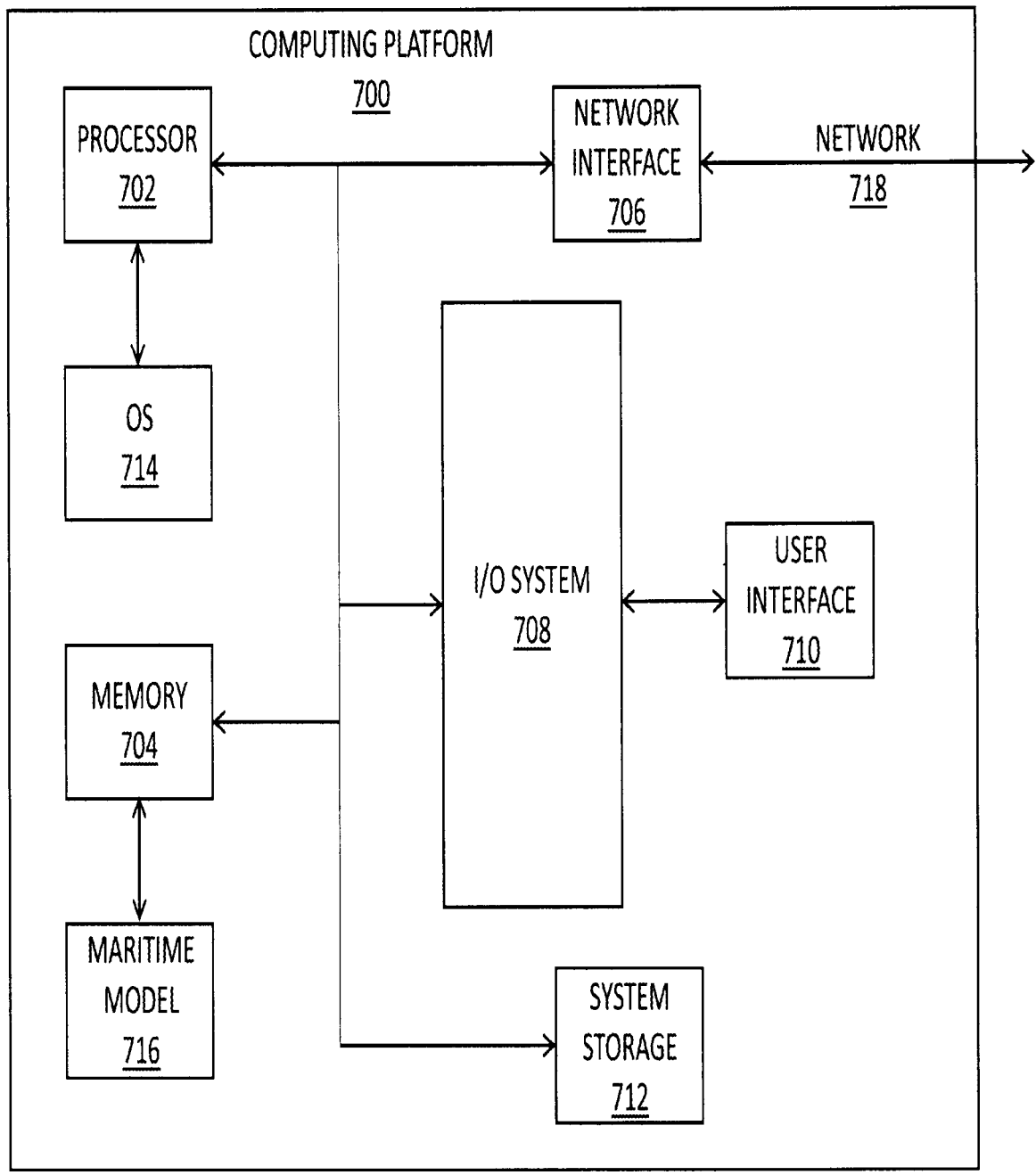
FIG. 7 illustrates a block diagram schematically illustrating a computing platform configured to update a maritime model, in accordance with some embodiments of the present disclosure.

FIG. 7 illustrates an example computing platform 700 that may be used to update or generate a maritime model 716, configured in accordance with certain embodiments of the present disclosure. In some embodiments, computing platform 700 may host, or otherwise be incorporated into any type of underwater vehicle, platform, or wearable device. In some other embodiments, computing platform 700 may be located in an on-land or on-ship processing center and configured to receive data from multiple measurement sources via network 718. Any combination of different devices may be used in certain embodiments.

In some embodiments, computing platform 700 may comprise any combination of a processor 702, a memory 704 configured to store a maritime model 716, a network interface 706, an input/output (I/O) system 708, a user interface 710, and a storage system 712. As can be further seen, a bus and/or interconnect is also provided to allow for communication between the various components listed above and/or other components not shown. Computing platform 700 can be coupled to a network 718 through network interface 706 to allow for communications with other computing devices, platforms, or resources. Other componentry and functionality not reflected in the block diagram of FIG. 7 will be apparent in light of this disclosure, and it will be appreciated that other embodiments are not limited to any particular hardware configuration.

Processor 702 can be any suitable processor and may include one or more coprocessors or controllers to assist in control and processing operations associated with computing platform 700. In some embodiments, processor 702 may be implemented as any number of processor cores. The processor (or processor cores) may be any type of processor, such as, for example, a micro-processor, an embedded processor, a digital signal processor (DSP), a graphics processor (GPU), a network processor, a field programmable gate array or other device configured to execute code. The processors may be multithreaded cores in that they may include more than one hardware thread context (or "logical processor") per core. In some embodiments, processor 702 performs some or all of the operations illustrated in method 600. Accordingly, processor 702 may perform operations to access and/or update maritime model 716 based on data received via network 718 (such as model update parameters).

Memory 704 can be implemented using any suitable type of digital storage including, for example, flash memory and/or random access memory (RAM). In some embodiments, memory 704 may include various layers of memory hierarchy and/or memory caches as are known to those of skill in the art. Memory 704 may be implemented as a volatile memory device such as, but not limited to, a RAM, dynamic RAM (DRAM), or static RAM (SRAM) device. Storage system 712 may be implemented as a non-volatile storage device such as, but not limited to, one or more of a hard disk drive (HDD), a solid-state drive (SSD), a universal serial bus (USB) drive, an optical disk drive, tape drive, an internal storage device, an attached storage device, flash memory, battery backed-up synchronous DRAM (SDRAM), and/or a network accessible storage device. In some embodiments, storage system 712 may comprise technology to increase the storage performance enhanced protection for valuable digital media when multiple hard drives are included.

Processor 702 may be configured to execute an Operating System (OS) 714 which may comprise any suitable operating system, such as Google Android (Google Inc., Mountain View, CA), Microsoft Windows (Microsoft Corp., Redmond, WA), Apple OS X (Apple Inc., Cupertino, CA), Linux, or a real-time operating system (RTOS). As will be appreciated in light of this disclosure, the techniques provided herein can be implemented without regard to the particular operating system provided in conjunction with computing platform 700, and therefore may also be implemented using any suitable existing or subsequently-developed platform.

Network interface 706 can be any appropriate network chip or chipset which allows for wired and/or wireless connection between other components of computing platform 700 and/or network 718, thereby enabling computing platform 700 to communicate with other local and/or remote computing systems, servers, cloud-based servers, and/or other resources. Wired communication may conform to existing (or yet to be developed) standards, such as, for example, Ethernet. Wireless communication may conform to existing (or yet to be developed) standards, such as, for example, cellular communications including LTE (Long Term Evolution), Wireless Fidelity (Wi-Fi), Bluetooth, and/or Near Field Communication (NFC). Exemplary wireless networks include, but are not limited to, wireless local area networks, wireless personal area networks, wireless metropolitan area networks, cellular networks, and satellite networks.

I/O system 708 may be configured to interface between various I/O devices and other components of computing platform 700. I/O devices may include, but not be limited to, a user interface 710. User interface 710 may include devices (not shown) such as a display element, touchpad, keyboard, mouse, and speaker, etc. I/O system 708 may include a graphics subsystem configured to perform processing of images for rendering on a display element. Graphics subsystem may be a graphics processing unit or a visual processing unit (VPU), for example. An analog or digital interface may be used to communicatively couple graphics subsystem and the display element. For example, the interface may be any of a high definition multimedia interface (HDMI), DisplayPort, wireless HDMI, and/or any other suitable interface using wireless high definition compliant techniques. In some embodiments, the graphics subsystem could be integrated into processor 702 or any chipset of computing platform 700. In some embodiments, user interface 710 may be used to graphically display various calculated parameters of maritime model 716.

It will be appreciated that in some embodiments, the various components of the computing platform 700 may be combined or integrated in a system-on-a-chip (SoC) architecture. In some embodiments, the components may be hardware components, firmware components, software components or any suitable combination of hardware, firmware or software.

In various embodiments, computing platform 700 may be implemented as a wireless system, a wired system, or a combination of both. When implemented as a wireless system, computing platform 700 may include components and interfaces suitable for communicating over a wireless shared media, such as one or more antennae, transmitters, receivers, transceivers, amplifiers, filters, control logic, and so forth. An example of wireless shared media may include portions of a wireless spectrum, such as the radio frequency spectrum and so forth. When implemented as a wired system, computing platform 700 may include components and interfaces suitable for communicating over wired communications media, such as input/output adapters, physical connectors to connect the input/output adaptor with a corresponding wired communications medium, a network interface card (NIC), disc controller, video controller, audio controller, and so forth. Examples of wired communications media may include a wire, cable metal leads, printed circuit board (PCB), backplane, switch fabric, semiconductor material, twisted pair wire, coaxial cable, fiber optics, and so forth.

The various embodiments disclosed herein can be implemented in various forms of hardware, software, firmware, and/or special purpose processors. For example, in one embodiment at least one non-transitory computer readable storage medium has instructions encoded thereon that, when executed by one or more processors, cause one or more of the signal transform methodologies disclosed herein to be implemented. The instructions can be encoded using a suitable programming language, such as C, C++, object oriented C, Java, JavaScript, Visual Basic .NET, Fortran 95, Fortran 2003, Fortran 2008, Beginner's All-Purpose Symbolic Instruction Code (BASIC), or alternatively, using custom or proprietary instruction sets. The instructions can be provided in the form of one or more computer software applications and/or applets that are tangibly embodied on a memory device, and that can be executed by a computer having any suitable architecture. In certain embodiments, the system may leverage processing resources provided by a remote computer system accessible via network 718. The computer software applications disclosed herein may include any number of different modules, sub-modules, or other components of distinct functionality, and can provide information to, or receive information from, still other components. These modules can be used, for example, to communicate with input and/or output devices such as a display screen, a touch sensitive surface, a printer, and/or any other suitable device. Other componentry and functionality not reflected in the illustrations will be apparent in light of this disclosure, and it will be appreciated that other embodiments are not limited to any particular hardware or software configuration. Thus, in other embodiments, computing platform 700 may comprise additional, fewer, or alternative subcomponents as compared to those included in the example embodiment of FIG. 7.

Some of the embodiments discussed herein may be implemented, for example, using a machine readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, process, or the like, and may be implemented using any suitable combination of hardware and/or software. The machine readable medium or article may include, for example, any suitable type of memory unit, memory device, memory article, memory medium, storage device, storage article, storage medium, and/or storage unit, such as memory, removable or non-removable media, erasable or non-erasable media, writeable or rewriteable media, digital or analog media, hard disk, floppy disk, compact disk read only memory (CD-ROM), compact disk recordable (CD-R) memory, compact disk rewriteable (CR-RW) memory, optical disk, magnetic media, magneto-optical media, removable memory cards or disks, various types of digital versatile disk (DVD), a tape, a cassette, or the like. The instructions may include any suitable type of code, such as source code, compiled code, interpreted code, executable code, static code, dynamic code, encrypted code, and the like, implemented using any suitable high level, low level, object oriented, visual, compiled, and/or interpreted programming language.

Unless specifically stated otherwise, it may be appreciated that terms such as "processing," "computing," "calculating," "determining," "estimating," or the like refer to the action and/or process of a computer or computing system, or similar electronic computing device, that manipulates and/or transforms data represented as physical quantities (for example, electronic) within the registers and/or memory units of the computer system into other data similarly represented as physical quantities within the registers, memory units, or other such information storage transmission or displays of the computer system. The embodiments are not limited in this context.

Numerous specific details have been set forth herein to provide a thorough understanding of the embodiments. It will be appreciated, however, that the embodiments may be practiced without these specific details. In other instances, well known operations, components and circuits have not been described in detail so as not to obscure the embodiments. It can be further appreciated that the specific structural and functional details disclosed herein may be representative and do not necessarily limit the scope of the embodiments. In addition, although the subject matter has been described in language specific to structural features and/or methodological acts, it is to be understood that the subject matter defined in the appended claims is not necessarily limited to the specific features or acts described herein. Rather, the specific features and acts described herein are disclosed as example forms of implementing the claims.

Further Example Embodiments

The following examples pertain to further embodiments, from which numerous permutations and configurations will be apparent.

Example 1 is an underwater sensing system that includes a cable structure, a water surface mount coupled to the cable structure, and at least one processor. The cable structure is configured to be deployed in a vertical orientation underwater. The cable structure comprises one or more sensors along a length of the cable structure, the one or more sensors configured to detect maritime data associated with one or more marine-based parameters in an underwater maritime region around the cable structure. The marine based parameters may include, for instance, water temperature, salt content of water, pressure of water at the depth pressure sensing is executed, and/or velocity of current within the water. The water surface mount is configured to be at least partially exposed above a surface of the underwater maritime region. The water surface mount comprises a transmitter configured to transmit the maritime data. The at least one processor is configured to receive the maritime data, access a maritime model comprising parameters associated with the underwater maritime region, and update the maritime model based on the maritime data. As will be appreciated, the parameters making up the model can be the one or more parameters sensed by the one or more sensors (e.g., temperature, salt content of water, pressure of water at the depth pressure sensing is executed, and/or velocity of current within the water).

Example 2 includes the subject matter of Example 1, wherein the one or more sensors comprises one or more thermistors.

Example 3 includes the subject matter of Example 1 or 2, wherein the one or more sensors comprises one or more salinity meters.

Example 4 includes the subject matter of any one of Examples 1-3, wherein the one or more sensors comprises one or more pressure sensors.

Example 5 includes the subject matter of any one of Examples 1-4, wherein the one or more sensors comprises one or more velocimeters.

Example 6 includes the subject matter of any one of Examples 1-5, wherein the water surface mount comprises a spar buoy.

Example 7 includes the subject matter of any one of Examples 1-6, wherein the processor is further configured to generate the maritime model.

Example 8 includes the subject matter of any one of Examples 1-7, wherein the processor updates the maritime model by updating parameters of the maritime model associated with the effects of long-period internal waves.

Example 9 includes the subject matter of any one of Examples 1-8, wherein the processor updates the maritime model by updating parameters of the maritime model associated with the effects of short-period internal waves.

Example 10 includes the subject matter of any one of Examples 1-9, wherein the processor is located externally from the cable structure and the water surface mount.

Example 11 includes the subject matter of Example 10, wherein the processor is located in an underwater vehicle.

Example 12 includes the subject matter of Example 11, further comprising a signal beacon deployable at least partially underwater, wherein the signal beacon is configured to receive model update data, the model update data being derived from the maritime data, and to acoustically transmit the model update data to the underwater vehicle.

Example 13 includes the subject matter of any one of Examples 1-12, wherein the one or more sensors comprises one or more acoustic receivers.

Example 14 is a method of updating a maritime model to account for the effects of long-period internal waves, the method comprising: measuring maritime data associated with an underwater maritime region using one or more sensors deployed underwater in the maritime region; receiving model update parameters at a processing unit, the model update parameters being derived from the maritime data;

accessing, using the processing unit, a maritime model comprising parameters associated with the underwater maritime region; and updating, using the processing unit, the maritime model using the model update parameters to account for the effects of the long-period internal waves on a propagating acoustic signal through the underwater maritime region.

Example 15 includes the subject matter of Example 14, wherein the processing unit is a first processing unit, and the method further comprises transmitting the maritime data to a second processing unit; deriving the model update parameters associated with the long-period internal waves based on the maritime data using the second processing unit; and transmitting the derived model update parameters to the first processing unit.

Example 16 includes the subject matter of Example 15, further comprising generating the maritime model using the second processing unit or the first processing unit.

Example 17 includes the subject matter of Example 16, wherein generating the maritime model comprises generating the maritime model based at least on point measurements, profile measurements, and surface-based measurements of the underwater maritime region.

Example 18 includes the subject matter of any one of Examples 14-17, wherein measuring maritime data comprises measuring temperature.

Example 19 includes the subject matter of any one of Examples 14-18, wherein measuring maritime data comprises measuring salinity level.

Example 20 includes the subject matter of any one of Examples 14-19, wherein measuring maritime data comprises measuring pressure.

Example 21 includes the subject matter of any one of Examples 14-20, wherein measuring maritime data comprises measuring velocity.

Example 22 includes the subject matter of any one of Examples 14-21, wherein receiving the model update parameters comprises receiving the model update parameters at an underwater vehicle housing the processing unit.

Example 23 is a method of updating a maritime model to account for the effects of short-period internal waves, the method comprising: measuring maritime data associated with an underwater maritime region using one or more sensors deployed in the underwater maritime region; receiving model update parameters at a processing unit, the model update parameters being derived from the maritime data; accessing, using the processing unit, a maritime model comprising parameters associated with the underwater maritime region; and updating, using the processing unit, the maritime model using the model update parameters to account for the effects of the short-period internal waves on a propagating acoustic signal through the underwater maritime region.

Example 24 includes the subject matter of Example 23, wherein the processing unit is a first processing unit, and the method further comprises transmitting the maritime data to a second processing unit; deriving the model update parameters associated with the short-period internal waves based on the maritime data using the second processing unit; and transmitting the derived model update parameters to the first processing unit.

Example 25 includes the subject matter of Example 24, further comprising generating the maritime model using the second processing unit or the first processing unit.

Example 26 includes the subject matter of Example 25, wherein generating the maritime model comprises generating the maritime model based at least on point measurements, profile measurements, and surface-based measurements of the given maritime region.

Example 27 includes the subject matter of any one of Examples 23-26, wherein measuring maritime data comprises measuring temperature.

Example 28 includes the subject matter of any one of Examples 23-27, wherein measuring maritime data comprises measuring salinity level.

Example 29 includes the subject matter of any one of Examples 23-28, wherein measuring maritime data comprises measuring pressure.

Example 30 includes the subject matter of any one of Examples 23-29, wherein measuring maritime data comprises measuring velocity.

Example 31 includes the subject matter of any one of Examples 23-30, wherein receiving the model update parameters comprises receiving the model update parameters at an underwater vehicle housing the processing unit.

The foregoing description of example embodiments of the present disclosure has been presented for the purposes of illustration and description. It is not intended to be exhaustive or to limit the present disclosure to the precise form disclosed. Many modifications and variations are possible in light of this disclosure. It is intended that the scope of the present disclosure be limited not by this detailed description, but rather by the claims appended hereto.

What is claimed is:

1. An underwater sensing system, comprising:
   a cable structure configured to be deployed in a vertical orientation underwater, the cable structure comprising one or more sensors along a length of the cable structure, the one or more sensors configured to detect maritime data associated with one or more marine-based parameters in an underwater maritime region around the cable structure;
   a water surface mount coupled to the cable structure and configured to be at least partially exposed above a surface of the underwater maritime region, wherein the water surface mount comprises a transmitter configured to transmit the maritime data; and
   at least one processor configured to
     receive the maritime data,
     access a maritime model comprising parameters associated with the underwater maritime region, and
     update the maritime model based on the maritime data;
   wherein the at least one processor updates the maritime model by updating parameters of the maritime model associated with the effects of long-period internal waves.

2. The underwater sensing system of claim 1, wherein the one or more sensors comprises one or more thermistors, salinity meters, pressure sensors, velocimeters, or acoustic receivers.

3. The underwater sensing system of claim 1, wherein the water surface mount comprises a spar buoy.

4. The underwater sensing system of claim 1, wherein the at least one processor is further configured to generate the maritime model.

5. The underwater sensing system of claim 1, wherein the at least one processor updates the maritime model by updating parameters of the maritime model associated with the effects of short-period internal waves.

6. The underwater sensing system of claim 1, wherein the at least one processor is located externally from the cable structure and the water surface mount.

7. The underwater sensing system of claim 1, further comprising a signal beacon deployable at least partially underwater, wherein the signal beacon is configured to receive model update data, the model update data being derived from the maritime data, and to acoustically transmit the model update data to an underwater vehicle.

8. A method of updating a maritime model to account for the effects of long-period internal waves, the method comprising:
    measuring maritime data associated with an underwater maritime region using one or more sensors deployed underwater in the maritime region;
    receiving model update parameters at a processing unit, the model update parameters being derived from the maritime data;
    accessing, using the processing unit, a maritime model comprising parameters associated with the underwater maritime region; and
    updating, using the processing unit, the maritime model using the model update parameters to account for the effects of the long-period internal waves on a propagating acoustic signal through the underwater maritime region.

9. The method of claim 8, wherein the processing unit is a first processing unit, and the method further comprises:
    transmitting the maritime data to a second processing unit;
    deriving the model update parameters associated with the long-period internal waves based on the maritime data using the second processing unit; and
    transmitting the derived model update parameters to the first processing unit.

10. The method of claim 9, further comprising generating the maritime model using the second processing unit or the first processing unit.

11. The method of claim 10, wherein generating the maritime model comprises generating the maritime model based at least on point measurements, profile measurements, and surface-based measurements of the underwater maritime region.

12. The method of claim 8, wherein measuring maritime data comprises measuring one or more of temperature, salinity level, pressure, or velocity.

13. The method of claim 8, wherein receiving the model update parameters comprises receiving the model update parameters at an underwater vehicle housing the processing unit.

14. A method of updating a maritime model to account for the effects of short-period internal waves, the method comprising:
    measuring maritime data associated with an underwater maritime region using one or more sensors deployed in the underwater maritime region;
    receiving model update parameters at a processing unit, the model update parameters being derived from the maritime data;
    accessing, using the processing unit, a maritime model comprising parameters associated with the underwater maritime region; and
    updating, using the processing unit, the maritime model using the model update parameters to account for the effects of the short-period internal waves on a propagating acoustic signal through the underwater maritime region.

15. The method of claim 14, wherein the processing unit is a first processing unit, and the method further comprises:
    transmitting the maritime data to a second processing unit;
    deriving the model update parameters associated with the short-period internal waves based on the maritime data using the second processing unit; and
    transmitting the derived model update parameters to the first processing unit.

16. The method of claim 15, further comprising generating the maritime model using the second processing unit or the first processing unit.

17. The method of claim 16, wherein generating the maritime model comprises generating the maritime model based at least on point measurements, profile measurements, and surface-based measurements of the given maritime region.

18. The method of claim 14, wherein measuring maritime data comprises measuring one or more of temperature, salinity level, pressure, or velocity.

19. The method of claim 14, wherein receiving the model update parameters comprises receiving the model update parameters at an underwater vehicle housing the processing unit.

* * * * *